(12) United States Patent
Qi et al.

(10) Patent No.: US 12,064,281 B2
(45) Date of Patent: Aug. 20, 2024

(54) METHOD AND SYSTEM FOR DENOISING CT IMAGES USING A NEURAL NETWORK

(71) Applicants: The Regents of the University of California, Oakland, CA (US); CANON MEDICAL SYSTEMS CORPORATION, Otawara (JP)

(72) Inventors: Jinyi Qi, Davis, CA (US); Nimu Yuan, Davis, CA (US); Jian Zhou, Vernon Hills, IL (US)

(73) Assignees: The Regents of the University of California, Oakland, CA (US); CANON MEDICAL SYSTEMS CORPORATION, Otawara (JP)

(*) Notice: Subject to any disclaimer, the term of this patent is extended or adjusted under 35 U.S.C. 154(b) by 372 days.

(21) Appl. No.: 16/938,463

(22) Filed: Jul. 24, 2020

(65) Prior Publication Data

US 2021/0290191 A1 Sep. 23, 2021

Related U.S. Application Data

(60) Provisional application No. 62/991,269, filed on Mar. 18, 2020.

(51) Int. Cl.
*G06T 5/00* (2006.01)
*A61B 6/00* (2006.01)
*G06N 3/08* (2023.01)

(52) U.S. Cl.
CPC .......... *A61B 6/5211* (2013.01); *A61B 6/5258* (2013.01); *A61B 6/542* (2013.01);
(Continued)

(58) Field of Classification Search
CPC . G06T 2207/20084; G06T 2207/20081; G06T 7/0012; G06T 2207/10072;
(Continued)

(56) References Cited

U.S. PATENT DOCUMENTS

2017/0311918 A1* 11/2017 Qi .......................... A61B 6/032
2018/0357753 A1* 12/2018 Lehtinen .............. G06N 3/0454
(Continued)

FOREIGN PATENT DOCUMENTS

EP            3404611 A1 * 11/2018 ........... G06K 9/6256
WO    WO-2020100136 A1 *  5/2020 ........... G06K 9/6264

OTHER PUBLICATIONS

Yuan N, Zhou J and Qi J 2019b Low-dose CT image denoising without high-dose reference images 15th International Meeting on Fully Three-Dimensional Image Reconstruction in Radiology and Nuclear Medicine vol. 11072 p. 110721C.
(Continued)

*Primary Examiner* — Ian L Lemieux
*Assistant Examiner* — Woo C Rhim
(74) *Attorney, Agent, or Firm* — Oblon, McClelland, Maier & Neustadt, L.L.P.

(57) ABSTRACT

First and second substantially independent identically distributed half scans are obtained; the first substantially independent identically distributed half scan is used as training data to train a machine learning-based system, and the second substantially independent identically distributed half scan is used as label data to train a machine learning-based system. This produces a trained machine learning-based system.

22 Claims, 23 Drawing Sheets
(9 of 23 Drawing Sheet(s) Filed in Color)

(52) U.S. Cl.
CPC ............... *G06N 3/08* (2013.01); *G06T 5/002* (2013.01); *G06T 2207/20081* (2013.01); *G06T 2207/20084* (2013.01)

(58) Field of Classification Search
CPC .......... G06T 2207/10081; G06T 5/002; G06T 2207/10116; G06T 2207/10132; G06T 11/008; G06T 2200/04; G06T 2207/10088; G06T 2207/10101; G06T 2207/10104; G06T 2207/20076; G06T 2207/30048; G06T 2211/424; G06T 5/50; G06T 7/735; G06V 10/82; G06V 10/454; G06V 2201/03; G06V 10/761; G06V 10/764; G06V 10/772; G06V 2201/031; G06V 30/194; A61B 6/5211; A61B 6/5258; A61B 6/542; A61B 6/5205; A61B 6/032; G06N 3/08; G06N 3/0445; G06N 3/0454; G06N 3/0472; G06N 3/0481

See application file for complete search history.

(56) References Cited

U.S. PATENT DOCUMENTS

| | | | | |
|---|---|---|---|---|
| 2019/0108441 | A1* | 4/2019 | Thibault | G06T 11/003 |
| 2019/0164288 | A1* | 5/2019 | Wang | G06T 5/005 |
| 2020/0065940 | A1* | 2/2020 | Tang | G06K 9/6256 |
| 2020/0118306 | A1* | 4/2020 | Ye | G06T 5/002 |
| 2022/0058803 | A1* | 2/2022 | Bhattacharya | G06T 5/50 |

OTHER PUBLICATIONS

Whiting, B R; Massoumzadeh, P; Earl, O A; O'Sullivan, J A; Snyder, D L; and Williamson, J F; 2006, Properties of preprocessed sonogram data in x-ray computed tomography Med. Phys. 33, 3290-303.

Snyder, D L; Hammoud, A M; and White, R L; 1993, Image recovery from data acquired with a charge-coupled-device camera JOSA A 10, 1014-23.

La Riviere, P J; 2005, Penalized-likelihood sonogram smoothing for low-dose CT Med. Phys. 32, 1676-83.

Elbakri, I A; and Fessler, J A; 2002, Segmentation-free statistical image reconstruction for polyenergetic X-ray computed tomography Proceedings IEEE International Symposium on Biomedical Imaging pp. 828-831.

Jain, V; and Seung, S; 2009, Natural image denoising with convolutional networks Advances in neural information processing systems pp. 769-776.

Zhao, H; Gallo, O; Frosio, I; and Kautz, J; 2016. Loss functions for image restoration with neural networks IEEE Trans. Comput. Imaging 3 47-57.

Wang, Z, et al., 2004, Image quality assessment: from error visibility to structural similarity, IEEE Trans. Image Process. 13 600-12.

Ronneberger O, Fischer P and Brox T 2015 U-Net: Convolutional Networks for Biomedical Image Segmentation 1-8.

Ioffe, S; and Szegedy, C; 2015, Batch Normalization: Accelerating Deep Network Training by Reducing Internal Covariate Shift Proceedings of the 32nd International Conference on Machine Learning Proceedings of Machine Learning Research vol. 37, ed F Bach and D Blei (Lille, France: PMLR) pp. 448-456.

Nair, V; and Hinton, G E; 2010, Rectified linear units improve restricted Boltzmann machines Proceedings of the 27th international conference on machine learning (ICML-10) pp. 807-814.

Martin Abadi et al 2015 (TensorFlow): Large-Scale Machine Learning on Heterogeneous Systems, 19 pages.

Kingma, D P; and Ba, J; 2014, Adam: A Method for Stochastic Optimization arXiv Prepr. arXiv1412.6980 1-15.

Elhamiasl, M; and Nuyts, J; 2019, Simulating lower-dose scans from an available CT scan 15th International Meeting on Fully Three-Dimensional Image Reconstruction in Radiology and Nuclear Medicine vol. 11072 p. 110720X.

Chen et al, Low-Dose CT With a Residual Encoder-Decoder Convolutional Neural Network, IEEE Trans Med Imaging, DOI:10.1109/TMI.2017.2715284.

Du et al, Stacked competitive networks for noise reduction in low-dose CT, PLOS One, https://doi.org/10.1371/journal.pone.0190069.

Fan et al, Quadratic Autoencoder for low-dose CT denoising, IEEE Trans Medical Imaging, DOI: 10.1109/TMI.2019.2963248.

Lehtinen J, Munkberg J, Hasselgren J, Laine S, Karras T, Aittala M and Aila T 2018 Noise2noise: Learning image restoration without clean data arXiv Prepr. arXiv1803.04189.

Gholizadeh-Ansari, M., Alirezaie, J. & Babyn, P. Deep Learning for Low-Dose CT Denoising Using Perceptual Loss and Edge Detection Layer. J Digit Imaging 33, 504-515 (2020). URL: https://doi.org/10.1007/s10278-019-00274-4.

Liang X, Chen L, Nguyen D, Zhou Z, Gu X, Yang M, Wang J and Jiang S 2019 Generating synthesized computed tomography (CT) from cone-beam computed tomography (CBCT) using CycleGAN for adaptive radiation therapy Phys. Med. Biol. 64 125002.

Krull A; Buchholz, T-O; and Jug, F; 2019, Noise2Void—Learning Denoising From Single Noisy Images The IEEE Conference on Computer Vision and Pattern Recognition (CVPR)).

Batson,; J and Royer, L; 2019, Noise2self: Blind denoising by self-supervision arXiv Prepr. arXiv1901.11365.

* cited by examiner

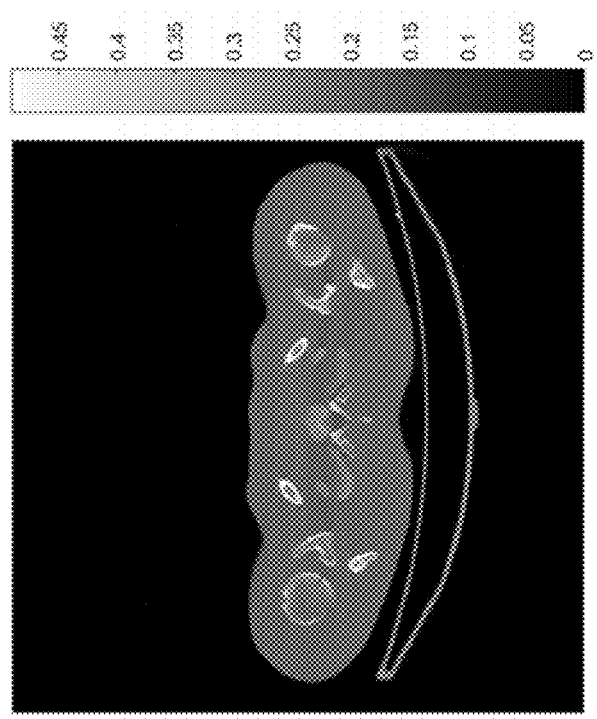
FIG. 3E
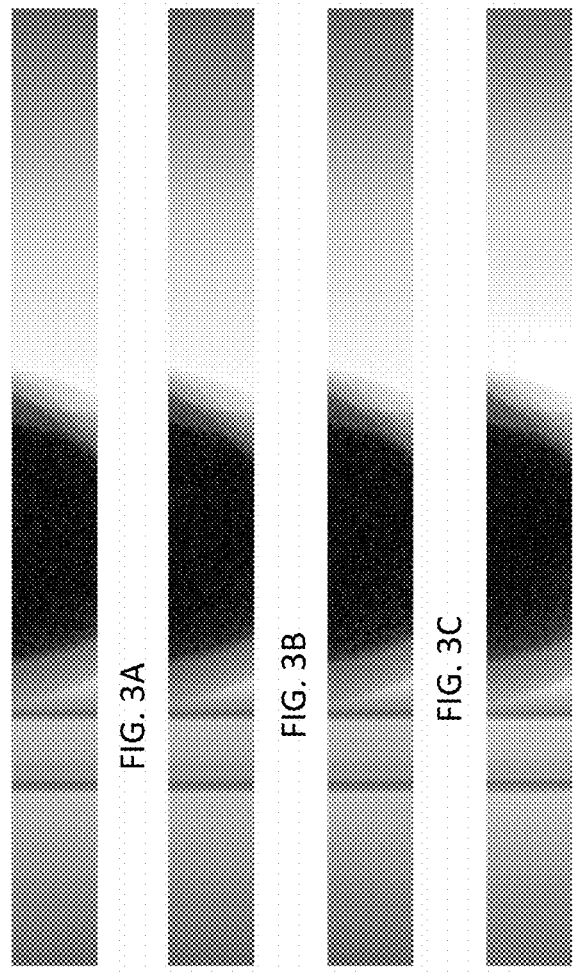
FIG. 3A
FIG. 3B
FIG. 3C
FIG. 3D

METHOD AND SYSTEM FOR DENOISING CT IMAGES USING A NEURAL NETWORK

CROSS REFERENCE TO APPLICATION

This application claims priority to U.S. Provisional Patent Application No. 62/991,269, filed Mar. 18, 2020, the contents of which are incorporated herein by reference.

FIELD OF THE INVENTION

The method and system described herein are directed to providing improved noise removal in images (e.g., medical images), and, in one embodiment, to a method and system for using deep neural network-based CT image denoising without independent reference data.

BACKGROUND

X-Ray computed tomography (CT) plays an important role in medical imaging, while the potential risk of radiation dose to patients cannot be ignored (Brenner and Hall 2007, Pearce et al 2012, de Gonzalez and Darby 2004). In order to reduce the radiation dose, a common approach is to decrease the tube current (Greess et al 2002). Unfortunately, lower dose introduces more noise and artifacts, which may deteriorate the diagnostic value of CT images.

Numerous methods have been proposed to reduce image noise. These methods can be divided into two main categories: (1) advanced iterative reconstruction methods (Geyer et al 2015, Tian et al 2011, Xu et al 2015) and (2) image processing methods, including both pre-processing projections or sinograms (Wang et at 2005, Manduca et al 2009) and post-processing reconstructed images (Feruglio et al 2010). Using iterative reconstruction techniques, the quality of reconstructed low-dose images can be substantially improved and can be comparable to the reconstructed images of high-dose CT (hdCT). However, iterative reconstruction techniques are usually time-consuming due to high computational complexity, and thus have not been commonly used in clinical practices. In comparison, image processing methods can be computationally faster, but they require a proper model of the noise, which can be difficult to obtain, and the resultant images may suffer from blurred edges and decreased resolution.

Recently, deep neural network (DNN) based image processing methods have been proposed (Chen et al 2017, Wang et al 2018, Kang et al 2018, Yuan et al 2019) and showed promising results. The standard way of training a denoising network is to take noisy low-dose CT (LdCT) images as the input and HdCT images as the reference. However, acquiring a large number of HdCT images is challenging due to the risk of radiation. In 2018, Lehtinen et al introduced a noise-to-noise (Noise2Noise) model to train DNNs without using any clean images. Previously, the Noise2Noise training was applied to LdCT denoising. See, e.g., [Yuan 2019b]: (Yuan N, Zhou J and Qi J 2019b Low-dose CT image denoising without high-dose reference images 15*th International Meeting on Fully Three-Dimensional Image Reconstruction in Radiology and Nuclear Medicine* vol 11072 p 110721C). Therein, the Low-dose-to-Low-dose (Ld2Ld) training achieved comparable results to Low-dose-to-High-dose (Ld2Hd) training in both count and image domains. However, Ld2Ld training requires an independent measurement as the reference, which means a repeated scan of the same subject is needed. Such repeated scans are not commonly available in practice.

SUMMARY

To address at least one problem identified with known techniques, the present disclosure describes a method and system that generates both training inputs and training labels from the same existing CT scans, and does not require any additional high-dose CT images or repeated scans of the same subject.

At least two substantially independent identically distributed partial-dose scans are obtained from a full-dose scan and used to train a machine learning-based system such as a neural network-based system. As used herein "substantially independent identically distributed partial-dose scans" may have a correlation coefficient of up to 0.05 between such scans. Alternatively, at least two nearly independent identically distributed partial-dose scans are obtained from a full-dose scan and used to train a machine learning-based system such as a neural network-based system. As used herein "nearly independent identically distributed partial-dose scans" may have a correlation coefficient of up to 0.02 between such scans. Alternatively, at least two virtually independent identically distributed partial-dose scans are obtained from a full-dose scan and used to train a machine learning-based system such as a neural network-based system. As used herein "virtually independent identically distributed partial-dose scans" may have a correlation coefficient of up to 0.01 between such scans. As used herein "completely independent identically distributed partial-dose scans" have a correlation coefficient of 0.0 between such scans. In light of the varying degrees of independence, in the disclosure herein, the scans generally shall be referred to as "independent identically distributed partial-dose scans" without a loss of generality.

In one embodiment, first and second independent identically distributed half-dose scans are obtained; the first independent identically distributed half-dose scan is used as training data to train a machine learning-based system, and the second independent identically distributed half-dose scan is used as label data to train a machine learning-based system. This produces a trained machine learning-based system. The machine learning-based system comprises a deep neural network, and the images are count-domain projections and/or image-domain reconstructed images. This method and system can be implemented in a number of technologies but generally relate to processing circuitry for performing the denoising described herein.

As used herein, "partial dose scans" are intended to include embodiments where less than all of the data of the full-dose scan is used in the "n" groups of data. For example, when using half-dose scans, each half-dose scan can include (n/2)*C data points, where C is a completeness measure for the partial-dose scan. When using a complete half-dose scan, C=1.0; however, C may be other values, for less complete data (e.g., C=0.95 for substantially complete half dose scans, C=.98 nearly complete half dose scans, and C=0.99 for virtually complete half dose scans). Thus, by extension, a virtually complete third-dose scan would include (n/3)*0.99 data points of the n full-dose data points. The various doses and the various amounts of independences may be grouped in any combination (e.g., using nearly independent identically distributed virtually complete partial-dose scans) without a loss of generalization.

Note that this summary section does not specify every embodiment and/or incrementally novel aspect of the present disclosure or claimed invention. Instead, this summary only provides a preliminary discussion of different embodiments and corresponding points of novelty. For additional details and/or possible perspectives of the invention and embodiments, the reader is directed to the Detailed Description section and corresponding figures of the present disclosure as further discussed below.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 3A is an image of a real 50 mAs projection of a shoulder phantom.

FIGS. 3B and 3C are simulated 50 mAs projections generated using the process of FIG. 1.

FIG. 3D is an image of a real 100 mAs projection of the shoulder phantom of FIG. 3A.

FIG. 3E is an image of a real high dose 300 mAs reconstructed shoulder phantom.

DETAILED DESCRIPTION

Figure 1:
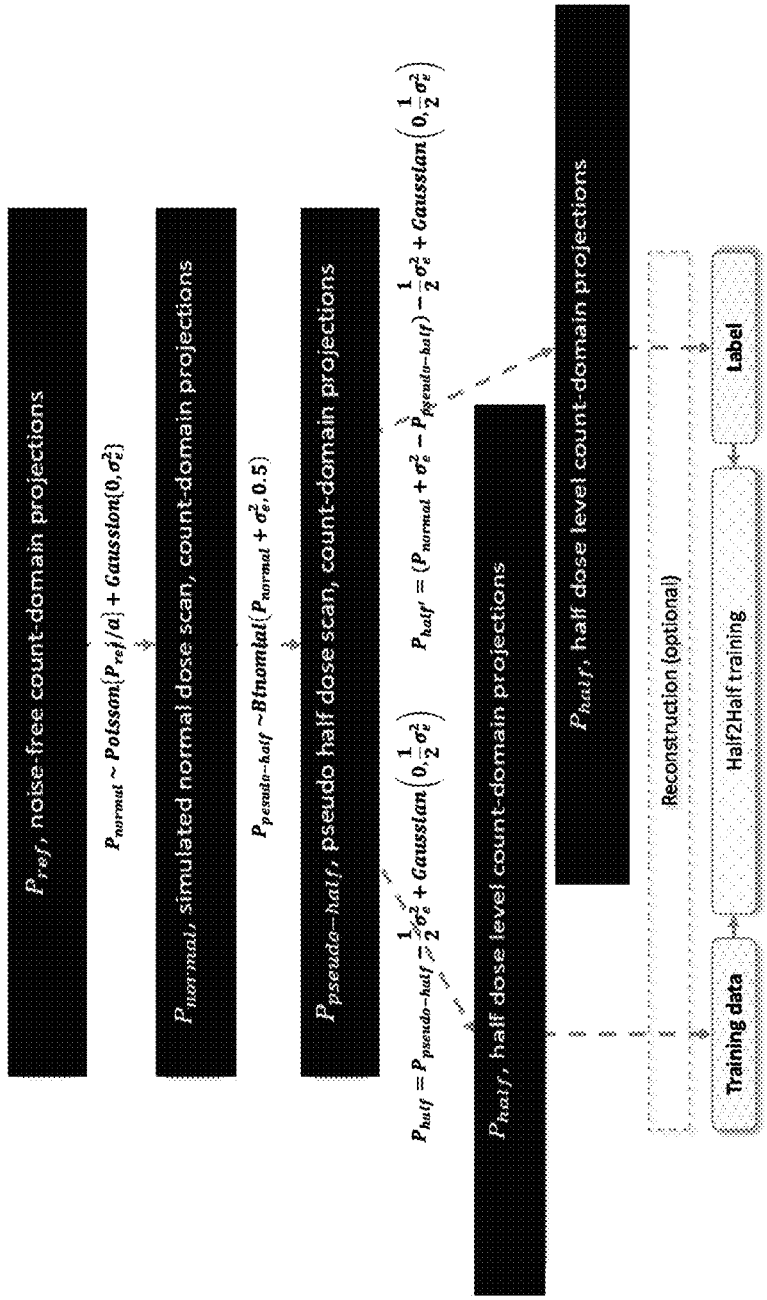
FIG. 1. is a dataflow diagram of a workflow of a training method for denoising images.

The following disclosure provides many different embodiments, or examples, for implementing different features of the provided subject matter. Specific examples of components and arrangements are described below to simplify the present disclosure. These are, of course, merely examples and are not intended to be limiting.

The order of discussion of the different steps as described herein has been presented for the sake of clarity. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present invention can be embodied and viewed in many different ways.

To reduce noise in an image processing system (e.g., a CT system), a method and system can be used to process captured images and remove various sources of noise. According to a method described herein, both the training data and the training label can be obtained from the same CT scan. Then the denoising network can be trained only using that data without any other high-dose CT (HdCT) data or repeated scan of the same subject. Since this method highly exploits the value of existing dataset and eliminates the requirement of either HdCT data or repeated scans for training a denoising neural network, it can be used as a tool for machine learning-based image denoising (e.g., deep neural network-based low-dose CT (LdCT) image denoising).

As described herein, a method of spitting original full-dose data into plural sets of independent partial-dose data will be described, and in one embodiment half-dose versions will be used; however, additional independent lower dose scans (e.g., thirds, fourths, etc.) can be used as well even if that means a portion of the data is not used. In general, for X-ray CT, a count-domain projection $P^{(I \cdot T)}$ (where I denotes the tube current of the acquisition and T denotes the exposure time) can be approximated by a combination of a compound Poisson distributed transmission noise and a white Gaussian electronic noise. (See, e.g., (1) [Whiting 2006]: (Whiting, B R; Massoumzadeh, P; Earl, O A; O'Sullivan, J A; Snyder, D L; and Williamson, J F; 2006, Properties of preprocessed sinogram data in x-ray computed tomography *Med Phys.* 33, 3290-303), (2) [Snyder 1993]: (Snyder, D L; Hammoud, A M; and White, R L; 1993, Image recovery from data acquired with a charge-coupled-device camera *JOSA A* 10, 1014-23), and (3) [La Riviere 2005]: (La Riviere, P J; 2005, Penalized-likelihood sinogram smoothing for low-dose CT *Med. Phys.* 32, 1676-83)). As described in [Elbakri/Fessler 2002]: (Elbakri, I A; and Fessler, J A; 2002, Segmentation-free statistical image reconstruction for polyenergetic X-ray computed tomography *Proceedings IEEE International Symposium on Biomedical Imaging* pp 828-31), the sum of the compound Poisson and Gaussian model can be approximated by a sum of the simple Poisson and Gaussian model according to:

$$P^{(I \cdot T)} \sim \text{Poisson}\{b_0 e^{-\rho}\} + \text{Gaussian}\{0, \sigma_e^2\} \tag{1}$$

where $b_0$ denotes the blank scan measurement, $\rho$ is the line integral of the linear attenuation coefficient of the scanned subject, and $\sigma_e$ denotes the standard deviation of electronic noise. In order to perform Noise2Noise training, the full-dose projection data $P^{(I \cdot T)}$ can be split into multiple (e.g., two) independent identically distributed partial-dose (e.g., half-dose) scans. In an embodiment using half-dose scans, each half-scan is acquired at $$\frac{t}{2}$$

current and exposure time T. The half-dose data should follow the Poisson plus Gaussian distribution $$P^{(\frac{1}{2} \cdot T)} \sim \text{Poisson}\left\{\frac{1}{2}b_0 e^{-P}\right\} + \text{Gaussian}\{0, \sigma_e^2\}$$

The process would be straightforward if the expectation of $P^{(I \cdot T)}$ was known, but only the noisy measurement is available. [Snyder 1993] shows that sum of the simple Poisson and Gaussian distribution can be approximated by a shifted Poisson distribution, such that:

$$P^{(I \cdot T)} + \sigma_e^2 \sim \text{Poisson}\{b_0 e^{-P} + \sigma_e^2\} \qquad (2)$$

Considering ($P^{(I \cdot T)} + \sigma_e^2$) as a Poisson process, a process can be used to split the measured data into two independent pseudo half-dose scans using:

$$P_{pseudo}^{(\frac{1}{2} \cdot T)} = \text{Binomial}\left(P^{(I \cdot T)} + \sigma_e^2, \frac{1}{2}\right), \qquad (3)$$

$$P_{pseudo}^{(\frac{1}{2} \cdot T)'} = P^{(I \cdot T)} + \sigma_e^2 - P_{pseudo}^{(\frac{1}{2} \cdot T)}. \qquad (4)$$

Each of them follows a Poisson distribution Poisson$\{\frac{1}{2}b_0 e^{-P} + \frac{1}{2}\sigma_e^2\}$. Equation (4) generates two independent datasets. If the binomial selection was used to generate both pseudo half-dose scans, the two datasets would not be independent but with a correlation coefficient of 0.5.

The variances of the pseudo half-dose scans are less than that of a true half-dose scan because the Gaussian noise component is also reduced in the splitting process. To compensate for the reduced Gaussian noise, an additional Gaussian noise with mean zero and variance $\frac{1}{2}\sigma_e^2$ can be added. The final two halt-dose scans are generated by the following formulae that compensate for both the mean and variance shifts:

$$P_{half} = P_{pseudo}^{(\frac{1}{2} \cdot T)} - \frac{1}{2}\sigma_e^2 + \text{Gaussian}\left\{0, \frac{1}{2}\sigma_e^2\right\} \qquad (5)$$

and $$P_{half'} = P_{pseudo}^{(\frac{1}{2} \cdot T)'} - \frac{1}{2}\sigma_e^2 + \text{Gaussian}\left\{0, \frac{1}{2}\sigma_e^2\right\} \qquad (6)$$

Equation (3) assumes that $P^{(I \cdot T)} + \sigma_e^2$ is a positive integer. For non-integer values, the binomial selection is applied to the integer part only and the fractional value is randomly assigned to one of the pseudo half scans.

The two half-dose scans generated from (3)-(6) are independent identically distributed and have the mean and variance matching the Poisson plus Gaussian model of a true half-dose scan. They can be used to train machine-based learning systems (e.g., artificial neural networks) for denoising low-dose CT images using a Noise2Noise training method. The training can be performed in either the count data domain or the image domain. For the count-domain training, one of the halfdose scans, $P_{half}$, is used as the training input and the other one, $P_{half'}$, as the label. For the image-domain training, the half-dose data, $P_{half}$ and $P_{half'}$, are reconstructed using the cone-beam filtered backprojection (FDK) method and then one of the reconstructed image is used as the training input and the other as the label. When using other partial dose scans, the number (n) of partial dose scans (e.g., n=3 for third-dose scans) allows n!/[2(n–2)!] combinations of pairs of inputs and training labels to be created. For third-dose scans, the number of combinations is (3!)/[2(3–2)!]=(6)/[2*1]=3 pairs of inputs and training labels. Assuming that the third-dose scans are A, B, and C, then the three pairs of inputs and training labels would be (A,B), (A, C), and (B,C), such that A is used as an input with B and C as training labels, and B is used as an input with C as a training label.

The mean absolute error (MAE) can be used as the loss function. (See, e.g., [Jain/Seung 2009]: (Jain, V; and Seung, S; 2009, Natural image denoising with convolutional networks *Advances in neural information processing systems* pp 769-76) and [Zhao 2016]: (Zhao, H; Gallo, O; Frosio, I; and Kautz, J; 2016. Loss functions for image restoration with neural networks *IEEE Trans. Comput. Imaging* 3 47-57)). Let $f_\theta$ denote a deep neural network with parameters $\theta$. The count-domain training tries to find $\theta$ that minimizes the selected loss function such as the following loss function:

$$\left\| f_\theta\left(P^{(\frac{1}{2} \cdot T)}\right) - P^{(\frac{1}{2} \cdot T)'} \right\|_1 \qquad (7)$$

For image-domain training, the objective function can be selected as the MAE between two FDK reconstructed images $$\left\| f_\theta\left(FDK\left(P^{(\frac{1}{2} \cdot T)}\right)\right) - FDK\left(P^{(\frac{1}{2} \cdot T)'}\right) \right\|_1 \qquad (8)$$

As described in greater detail below, to evaluate the effectiveness of the splitting process, a shoulder phantom was scanned at 50 mAs and 100 mAs dose levels with the x-ray tube and the detector remaining stationary. Each scan has 1,200 independent measurements of one projection view. Using what will be referred to as a "Half2Half" splitting model, two simulated 50 mAs datasets were generated from the real 100 mAs scan using equations (3)-(6) and the histogram of the counts in selected pixels are compared with those from the real 50 mAs scan. The spatial correlation between pixels in the simulated and real 50 mAs scans were also examined. However, as would be appreciated by those of skill in the art, splitting amounts other than halves can be used as well.

The general training evaluation workflow process is shown in FIG. 1. Real HdCT scans were acquired from five subjects using helical CT scanners. They were considered as noise-free reference data. Normal-dose data were simulated from that reference HdCT data using the Poisson+Gaussian model in (1). The dose levels of all the training and testing datasets are shown below in Table 1.

TABLE 1

| | Half2Half half dose level | Ld2Ld/Ld2Hd at half dose level | Ld2Ld/Ld2Hd at normal dose level |
|---|---|---|---|
| Training dataset | 15.0~50.7 | 15.0~50.7 | 30.0~101.4 |
| Validation dataset | 35.0 | 35.0 | 70.0 |
| Simulated test dataset | | 17.5. 35.0. 52.5 70.0. 105.0 and 140.0 | |
| Real LdCT test dataset | | 40.0. 63.0 and 75.0 | |

The tube voltage of all scans was 120 kVp. After that, half-dose training data were generated by splitting the full-dose (also referred to as the normal-dose) data using the model in (3)-(6). The half-dose data were used to training denoising neural networks in either the count domain or the image domain.

The HdCT scans were split into three subsets: (1) a training dataset including three subject scans used for training, (2) a validation dataset including a single subject scan, and (3) a test dataset reserved for testing.

Training dataset: For each subject, three different dose levels were simulated, resulting in a total of nine scans in the training dataset. The normal-dose training data had dose levels between 30.0 and 101.4 mAs and the half-dose training data were between 15.0 and 50.7 mAs. In the count-domain training, there were a total of 54,000 projections (896×80 pixels each), but only half of them were used due to a limit on the computer memory in the training system. In the image domain training, there were a total of 5,175 image slices (512×512 pixels each) and all were used.

Validation dataset: This dataset was only used for monitoring the training process and tuning training parameters. Thus, the dose levels were chosen to be close to the mean dose level of the training dataset. The dose level was around 70.0 mAs for the normal-dose training and 35.0 mAs for the half-dose training.

Test dataset: The test dataset had six different dose levels, ranging from 17.5 to 140.0 mAs. In addition to the simulation data, three real LdCT scans, which had dose levels between 40.0 and 75.0 mAs, were also acquired and used to test the network performances.

For comparison, Noise2Noise training using independent identically distributed data generated by the Poisson+Gaussian model was used in (1) at both a half dose level and a normal dose level. These network trainings are referred to as Ld2Ld. The network was also trained using the high-dose reference data as the label, which is referred to as Ld2Hd training. MAE, Signal-to-Noise Ration (SNR) and Structural Similarity index (SSIM) (see [Wang 2004]: (Wang, Z, et al., 2004, Image quality assessment: from error visibility to structural similarity, *IEEE Trans. image Process.* 13 600-12)) were used to evaluate the performance of the denoised images from the trained networks.

Figure 2:
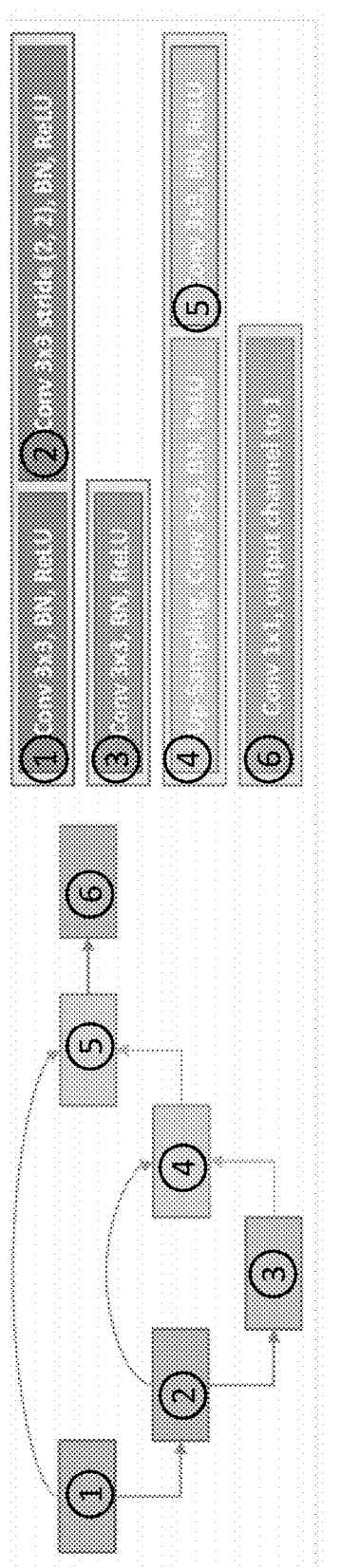
FIG. 2 is a block diagram of an architecture (e.g., having a U-net structure) for denoising images.

As shown in FIG. 2, a U-Net structure (see, e.g., [Ronneberger 2015]: (Ronneberger O, Fischer P and Brox T 2015 U-Net: Convolutional Networks for Biomedical Image Segmentation 1-8)) was used that has an encoder-decoder architecture. The network includes a series convolution, down-sampling, and up-sampling layers with skip connections. The kernel size is 3×3 in all convolutional layers except in the last one, where the kernel size is 1×1. The root filter number is 64 and the number is doubled after each down-sampling process. Batch Normalization (BN) and Rectified Linear Units (ReLU) are used after each convolutional layer. For details on Batch Normalization (BN), see, e.g., [Ioffe/Szegedy 2015]: (Ioffe, S; and Szegedy, C; 2015, Batch Normalization: Accelerating Deep Network Training by Reducing Internal Covariate Shift *Proceedings of the 32nd International Conference on Machine Learning* Proceedings of Machine Learning Research vol 37, ed F Bach and D Blei (Lille, France: PMLR) pp 448-56)). For details on Rectified Linear Units (ReLU), see, e.g., [Nair/Hinton 2010]: (Nair, V; and Hinton, G E; 2010, Rectified linear units improve restricted boltzmann machines *Proceedings of the 27th international conference on machine learning (ICML-10)* pp 807-14). This modified U-Net has only two down-sampling layers and two up-sampling layers (depth-3). The network input has three channels (the central projection/slice plus two adjacent projections/slices). For the count-domain denoising, the input size is 896×80×3 and for the image-domain denoising, the input size is 512×512×3.

Test networks were implemented using Tensorflow 1.8.0 (see, e.g., [Abadi 2015]: (Martín Abadi et al 2015 {Tensor-Flow}: Large-Scale Machine Learning on Heterogeneous Systems) and Keras 2.2.4 (https://keras.io) and trained using an NVIDIA GeForce GTX 1080Ti GPU. For each training, the adaptive moment estimation (ADAM) technique was used as the optimizer. (See, e.g., [Kingma/Ba 2014]: (Kingma, D P; and Ba, J; 2014, Adam: A Method for Stochastic Optimization *arXiv Prepr. arXiv*1412.6980 1-15).) The initial learning rate was 0.001, which was then adaptively reduced by 80% once the training loss stopped reducing for 20 epochs. The number of total epochs in each training was 1000.

Representative real and split projections and a high-dose reconstructed slice of shoulder phantom are shown in FIGS. 3A-3E.

Figure 4:
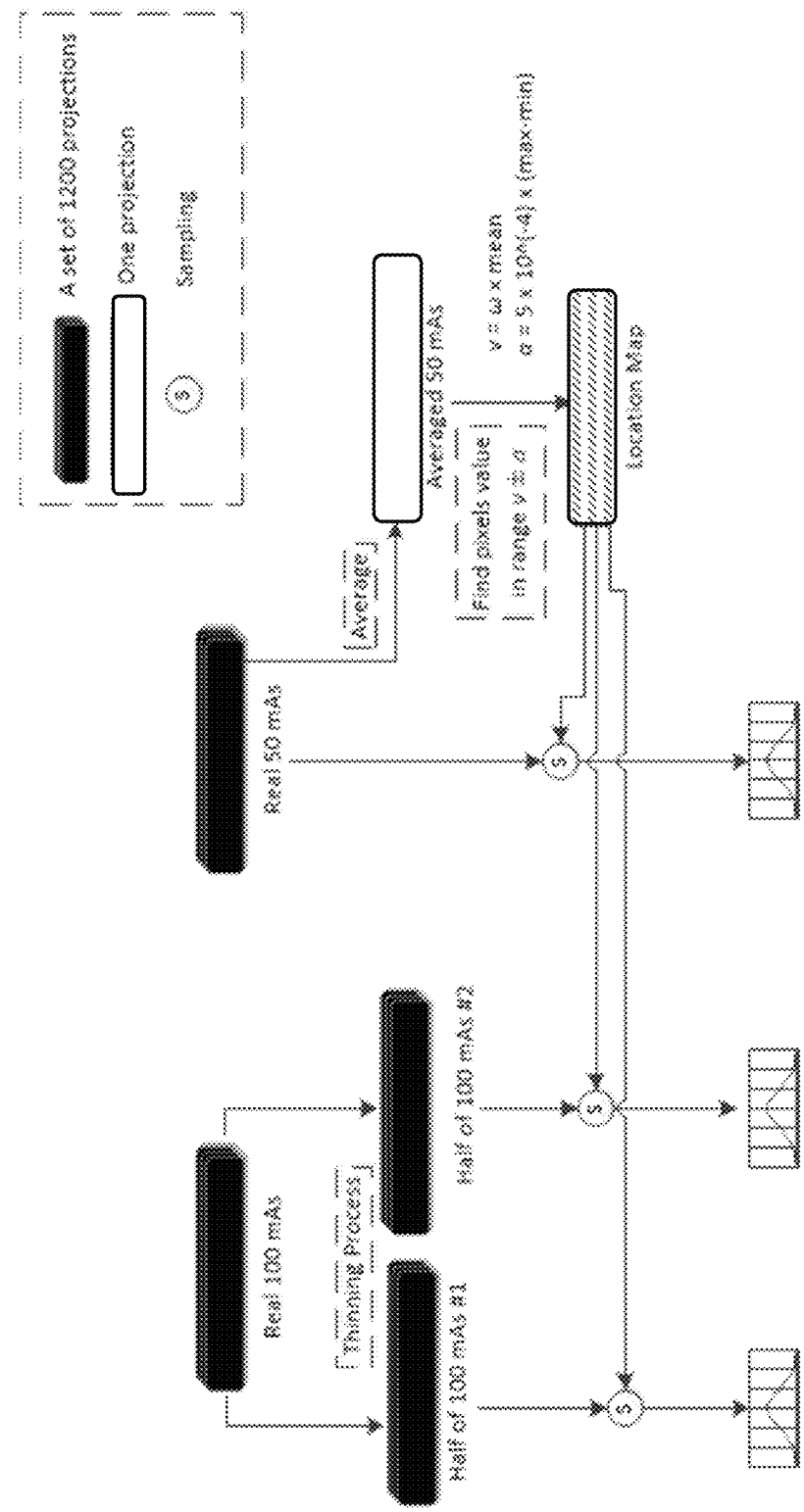
FIG. 4 is a workflow for sampling pixels and producing histograms as part of the denoising process.
Figure 5A:
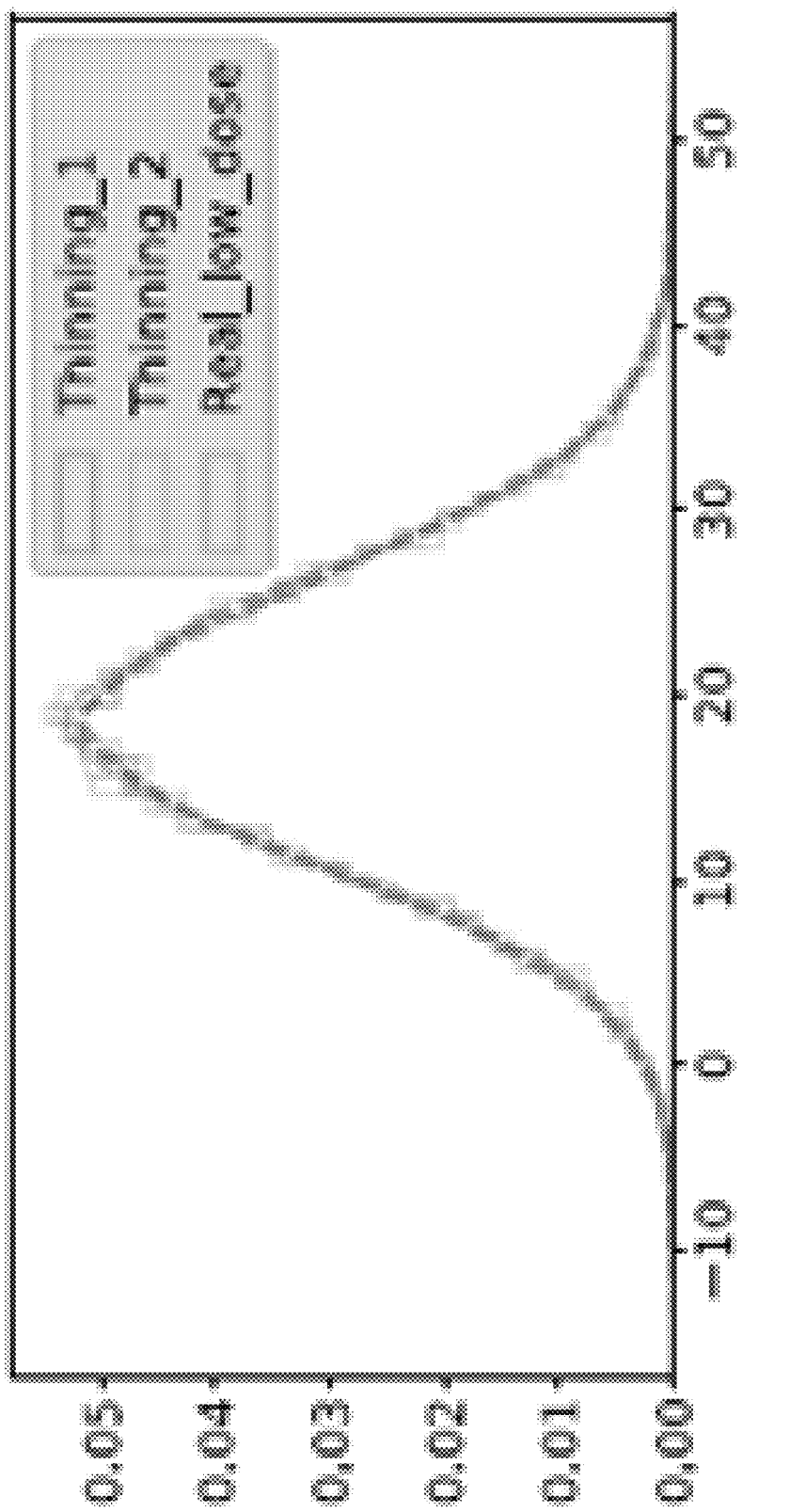
FIGS. 5A to 5I are a series of histograms of data generated from an exemplary thinning process and real low-dose scan.
Figure 5B:
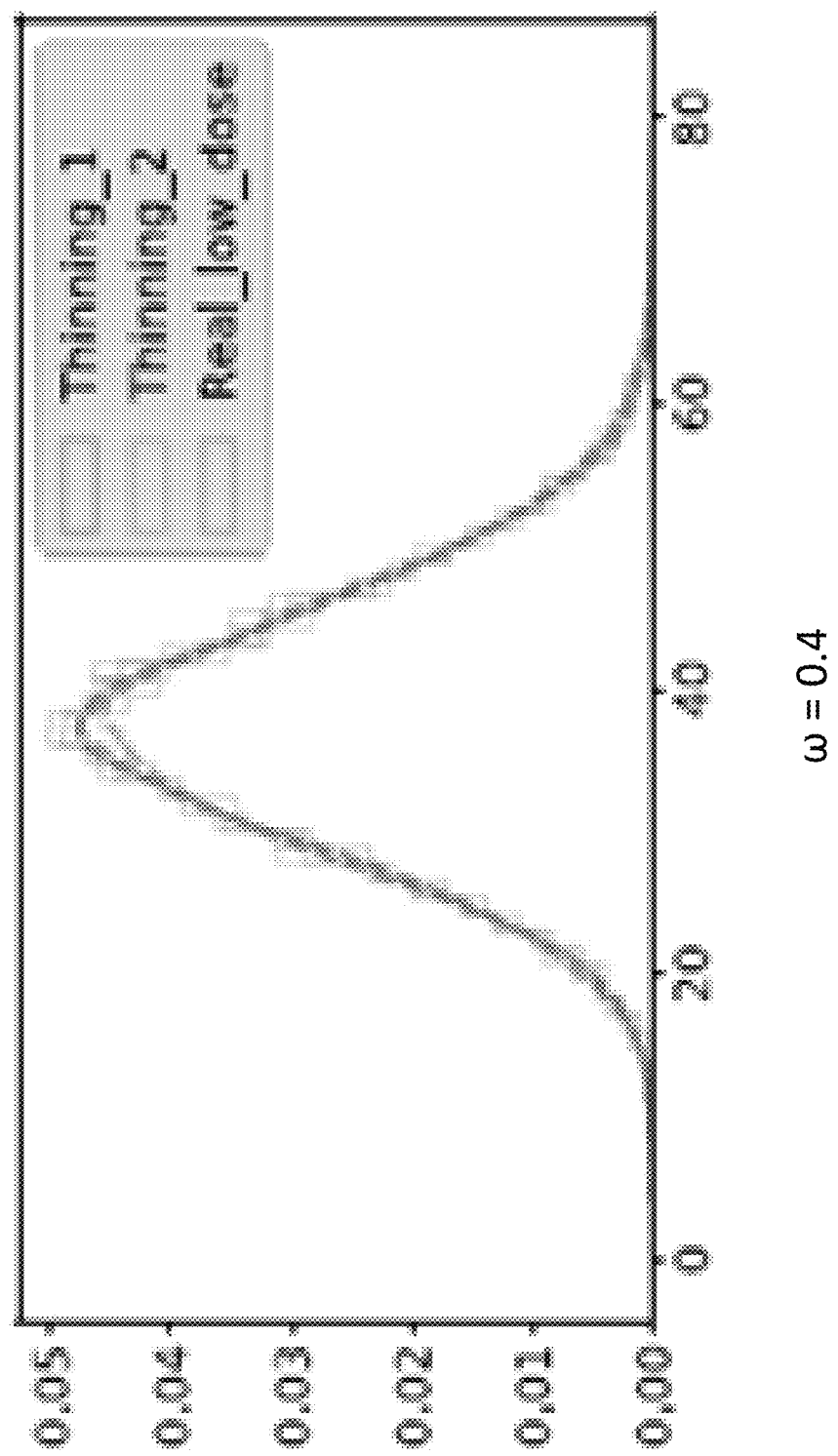
Figure 5C:
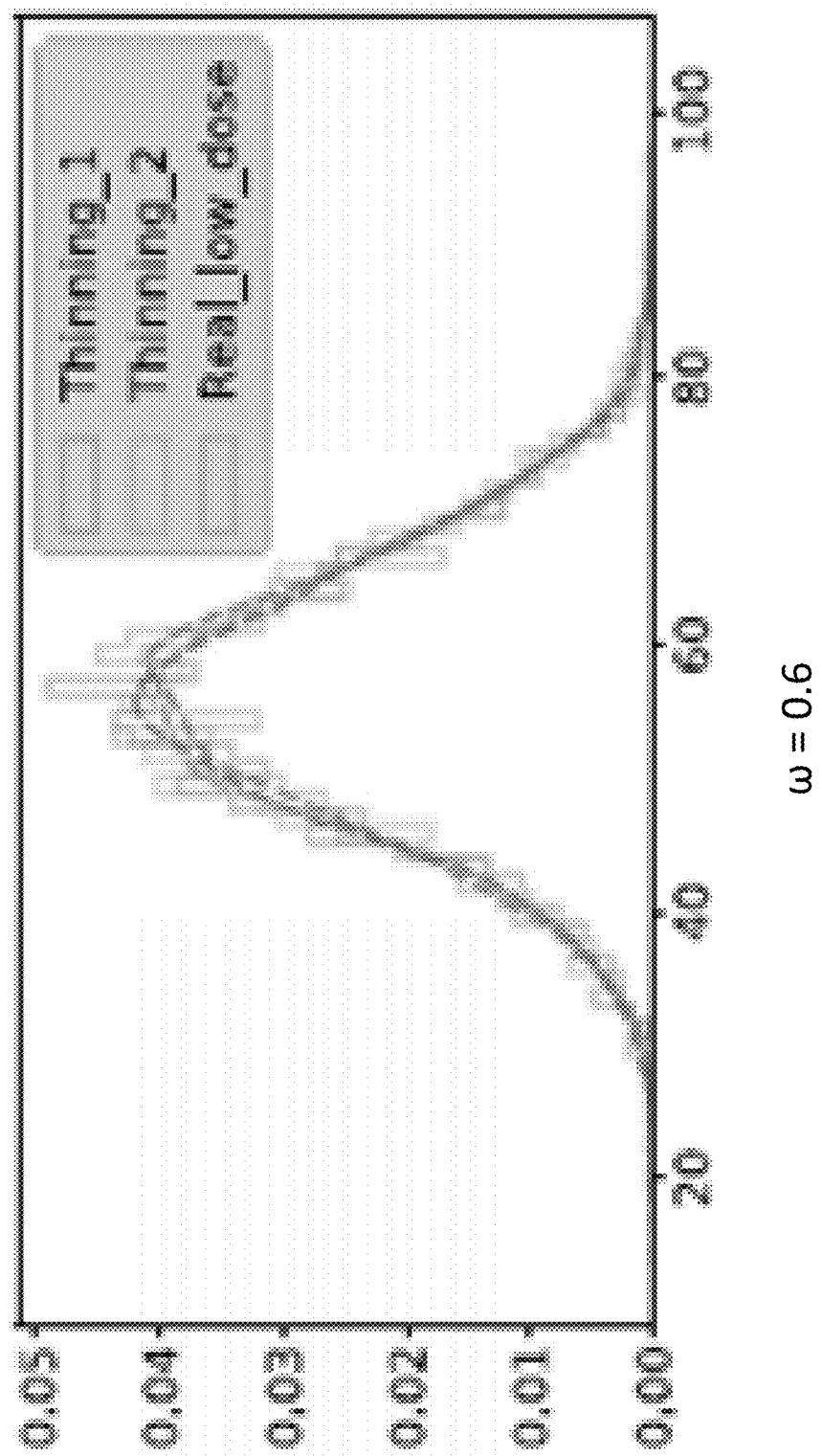
Figure 5D:
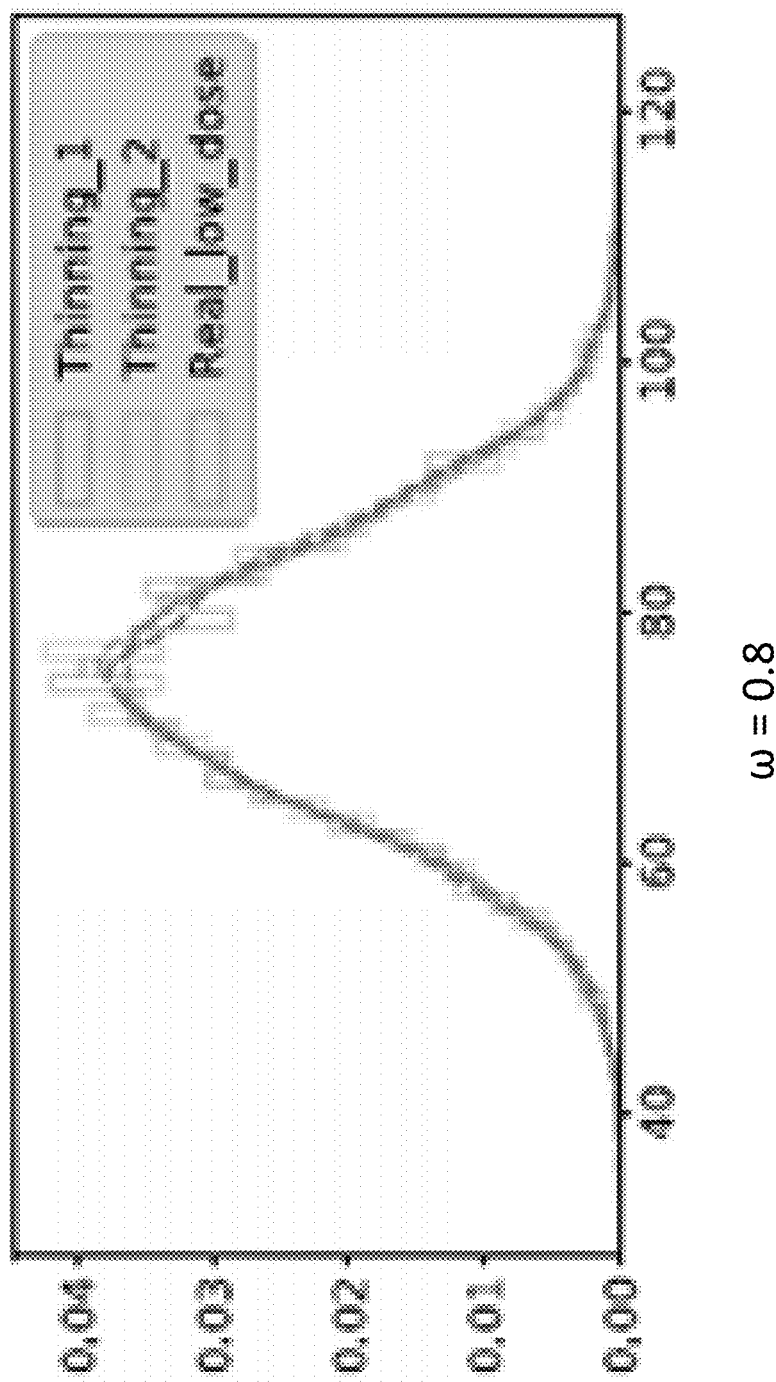
Figure 5E:
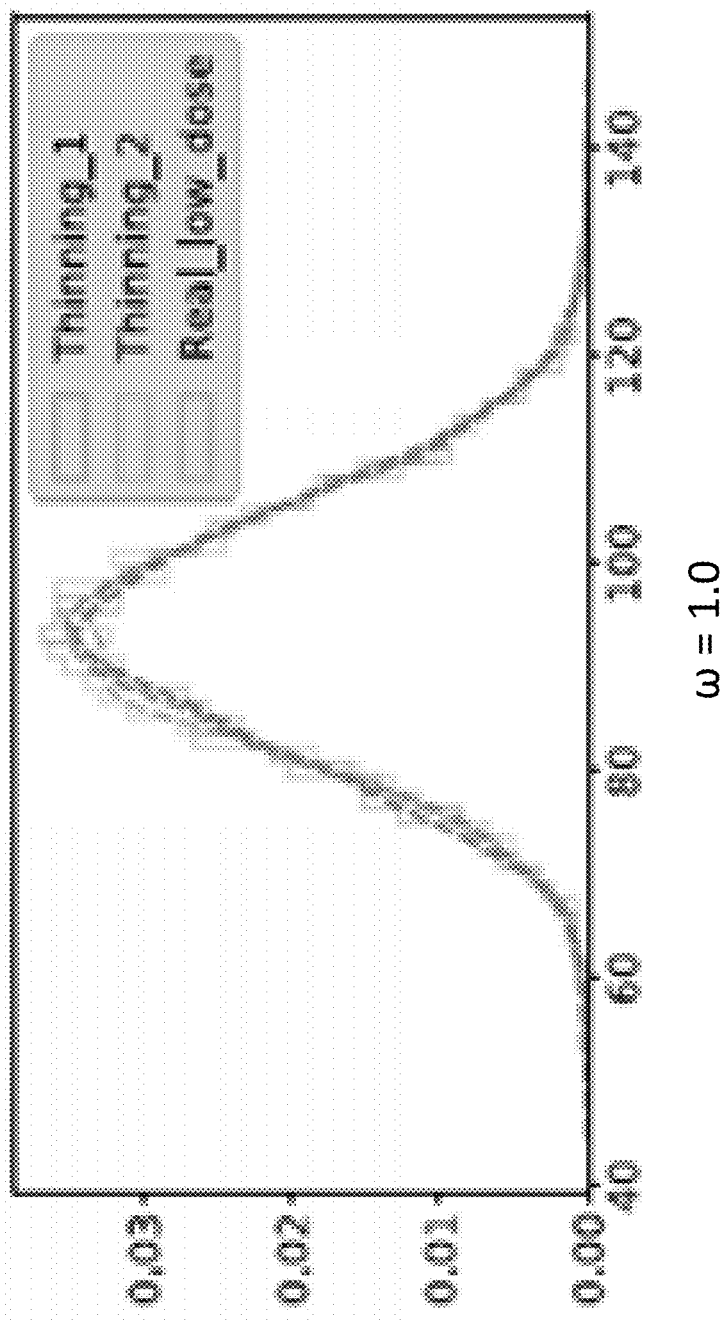
Figure 5F:
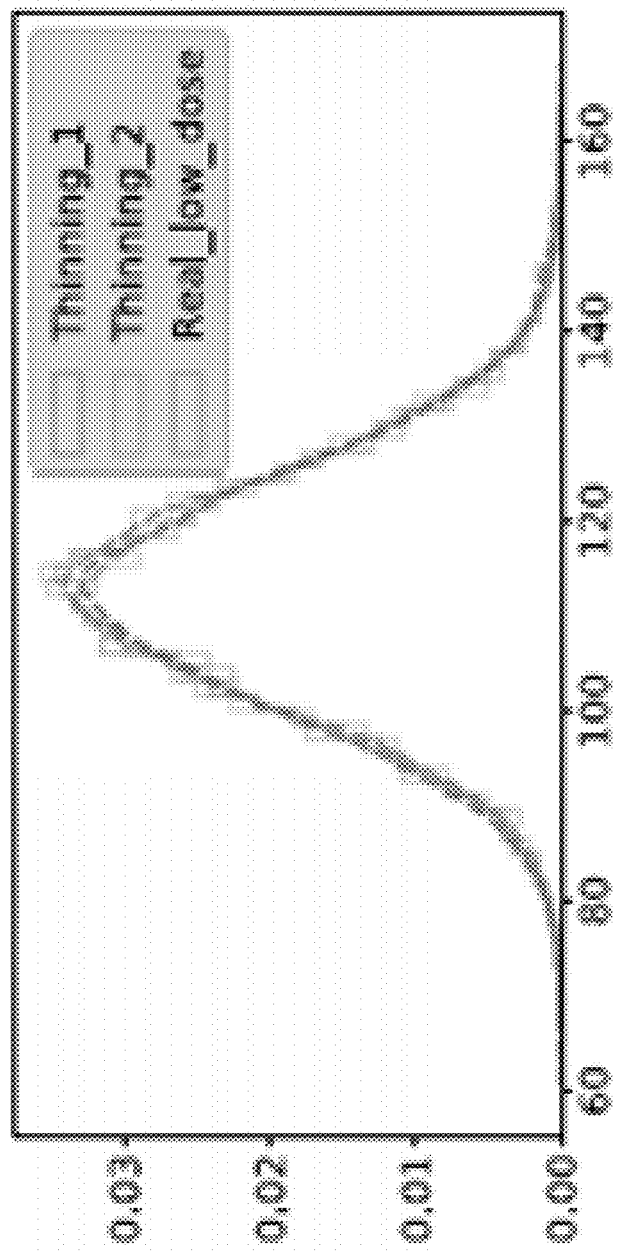
Figure 5G:
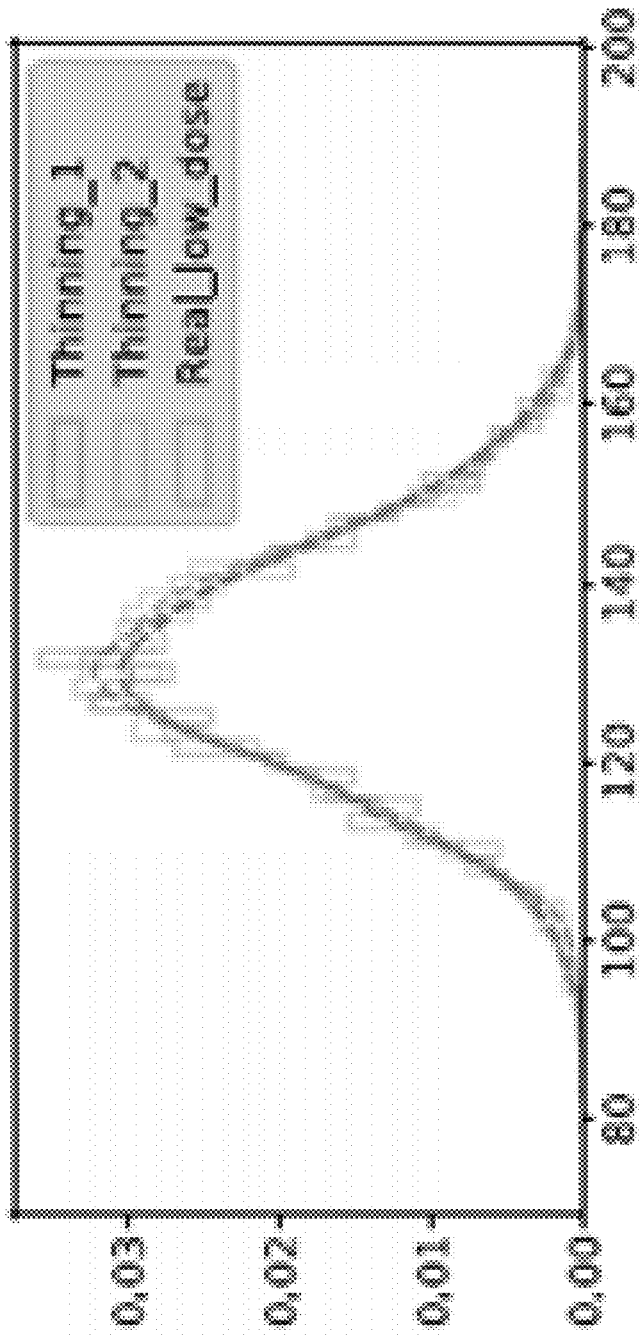
Figure 5H:
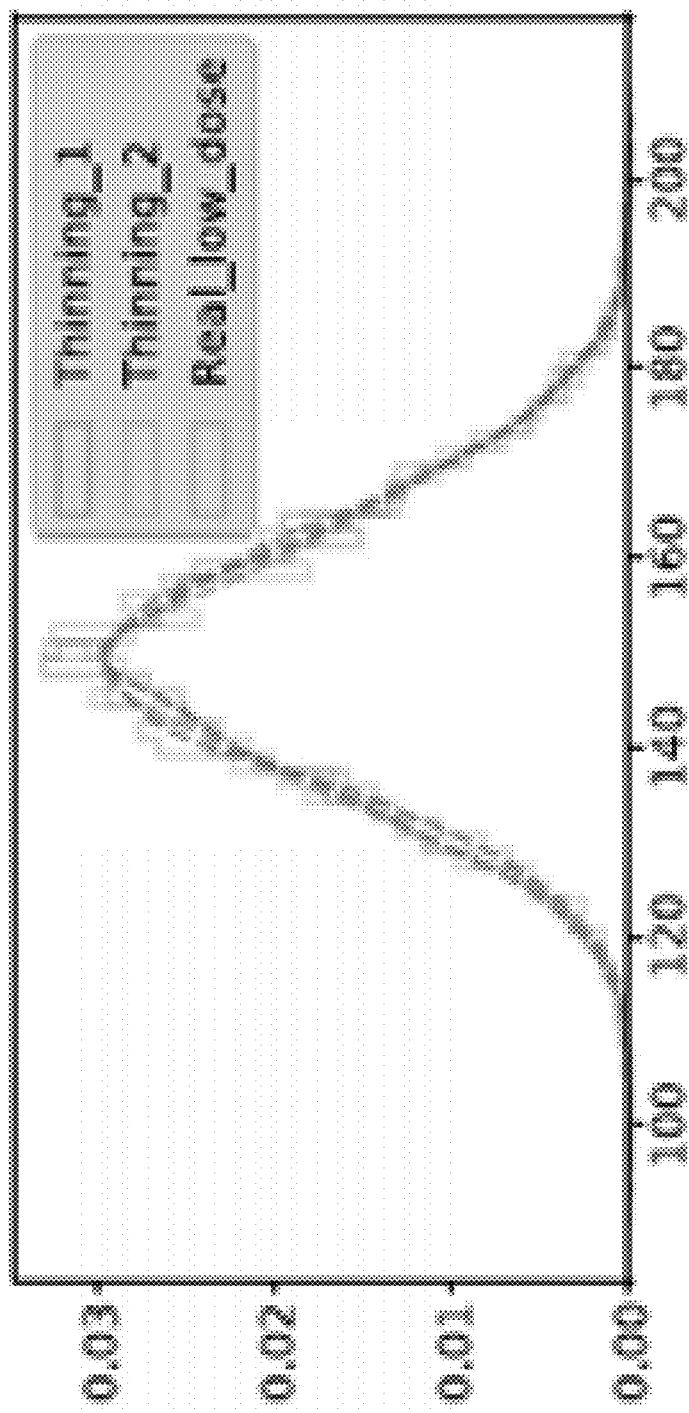
Figure 5I:
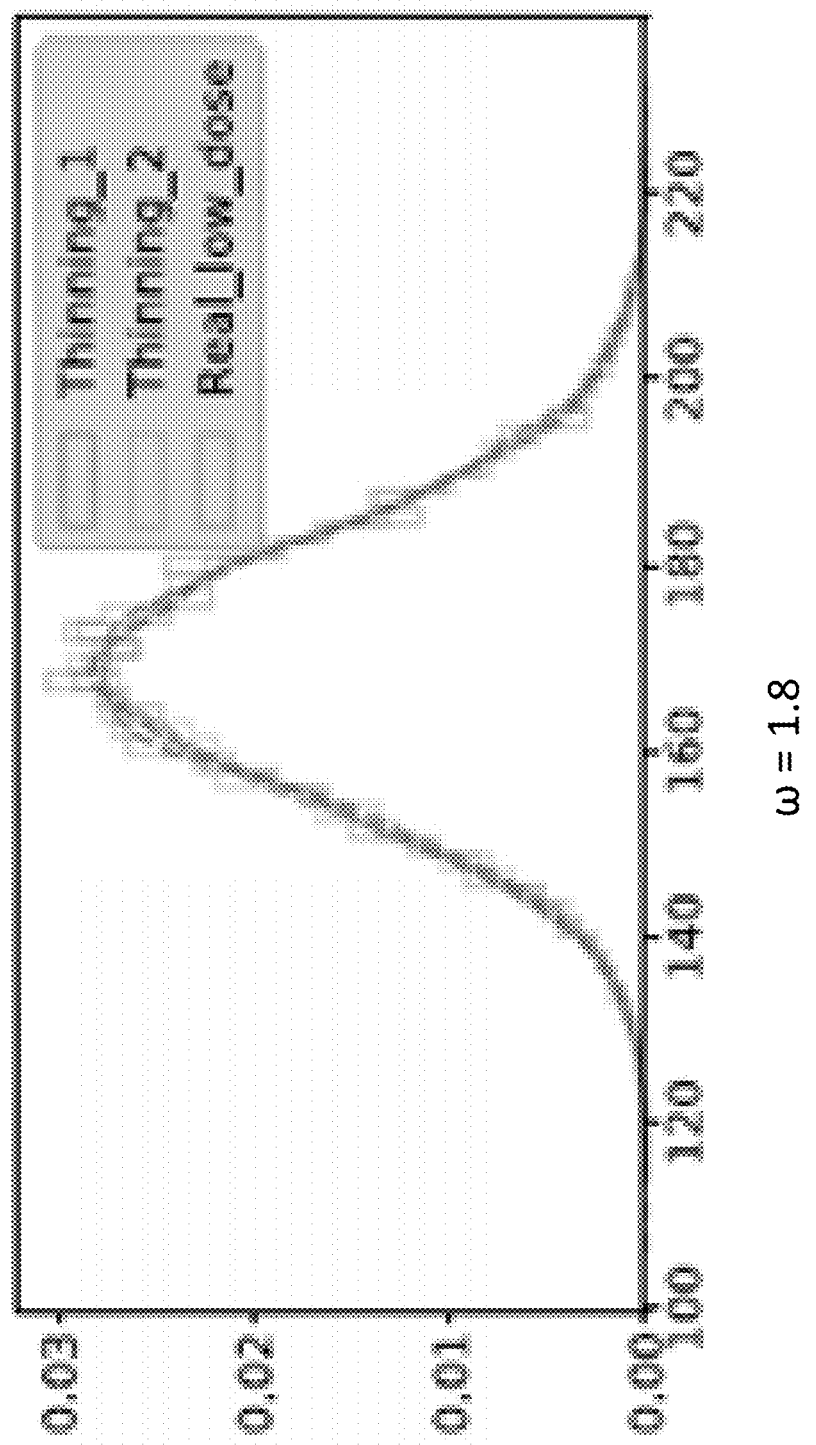

The histogram of the real 50 mAs scans and simulated 50 mAs scans are compared for a number of selected pixels. The flow chart is shown in FIG. 4. To increase the number of samples, detector pixels with a similar mean values were grouped together. A range of $\alpha=5\times10^{-4}\times(max-min)$ was used, where max and min are the maximum and minimum pixel values in the projection. FIGS. 5A-5I compare the histograms of real 50 mAs scans (purple curves) and simulated 50 mAs scans generated by the splitting process (blue and orange curves) for selected pixels. The solid curves denote the raw histograms and the dashed ones are fitted curves. The weighting factor $\omega$ represents the ratio between the mean of the pixel counts and the mean of the whole projection and was chosen from 0.2 to 1.8. The results show that the splitting process produces half-dose data with histograms matching well with those of real low-dose scans for a wide range of count levels.

It was reported that noise of two neighboring pixels can be correlated due to crosstalk. See, e.g., [Elhamiasl/Nuyts 2019]: (Elhamiasl, M; and Nuyts, J; 2019, Simulating lower-dose scans from an available CT scan *15th International Meeting on Fully Three-Dimensional Image Reconstruction in Radiology and Nuclear Medicine* vol 11072 p 110720X). The splitting process reduces the spatial correlation and may cause non-negligible errors. The noise correlation coefficient was calculated between neighboring pixels in the real 50 mAs and simulated 50 mAs datasets and the results are shown in Table 2. Although the correlation coefficients of the Half2Half dataset are indeed less than that of the real 50 mAs scan, all the coefficients in the tested data are close to zero and small enough to be ignored. Therefore, no compensation for the spatial correlation is used in a first embodiment of the splitting process. However, in an alternative embodiment compensation for the spatial correlation is used in the splitting process.

TABLE 2

Averaged noise correlation coefficient between neighboring pixels.

| Dataset | Noise correlation coefficients |
|---|---|
| Real 50 mAs scan | 0.0202 |
| Half of 100 mAs scan #1 | 0.0085 |
| Half of 100 mAs scan #2 | 0.0085 |

Figure 6:
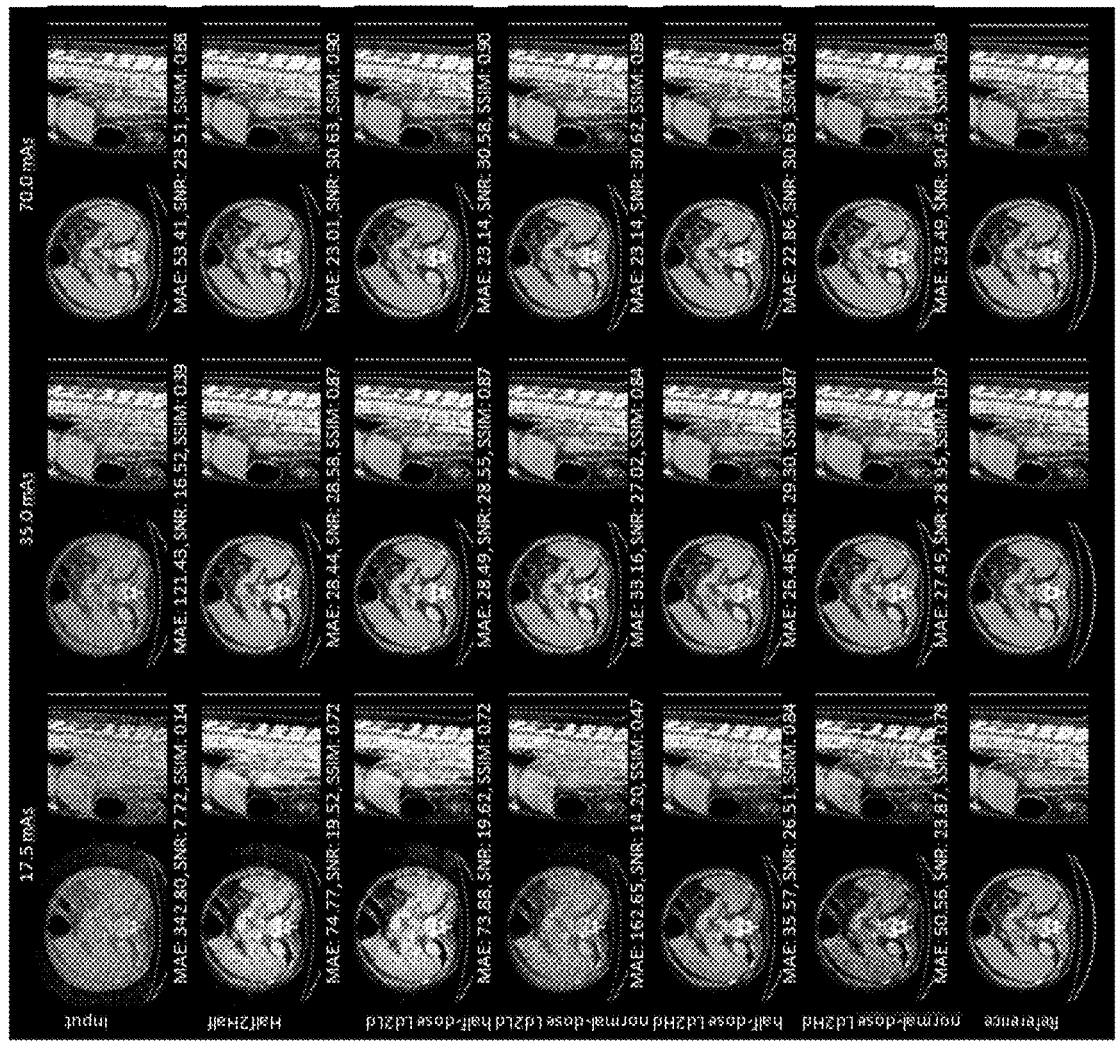
FIG. 6 is a series of images representing count-domain denoised results of simulated test data.

In an embodiment using count-domain denoising, all the denoised count-domain projections were reconstructed by the FDK technique. Representative transaxial and sagittal slices of denoised images from the simulated testing dataset are shown in FIG. 6. The display window is W=400HU, L=40HU. The SNR and SSIM of each image are listed at the bottom of each panel. All the denoising methods offered significant SNR and SSIM gains over the inputs. The MAE, SNR and SSIM of the complete test dataset are listed in the Table 3.

Comparing with Ld2Ld and Ld2Hd training at the half-dose level, Half2Half training provided similar results in terms of MEA, SNR and SSIM; comparing with Ld2Ld and Ld2Hd training at the normal-dose level, Half2Half training only performed worse at the highest dose level of the test data (140.0 mAs) because the dose level was outside the range of the training data. For the same reason, at the lowest dose level (17.5 mAs), normal-dose Ld2Ld and Ld2Hd could not suppress the streaky artifacts effectively and showed worse performance than the Half2Half training result.

TABLE 3

Quantitative comparison of different count-domain methods the on simulated test dataset. (Bold face texts denote the best score in each column.)

| 17.5 mAs | 35.0 mAs | 52.5 mAs | 70.0 mAs | 105.0 mAs | 140.0 mAs |
|---|---|---|---|---|---|
| | | | Input | | |
| MAE: 342.80 | MAE: 121.43 | MAE: 70.20 | MAE: 53.41 | MAE: 39.51 | MAE: 32.65 |
| SNR: 7.72 | SNR: 13.52 | SNR: 21.16 | SNR: 23.51 | SNR: 26.11 | SNR: 27.75 |
| SSIM: 0.14 | SSIM: 0.39 | SSIM: 0.49 | SSIM: 0.68 | SSIM: 0.78 | SSIM: 0.83 |
| | | Half2Half training (15.0~50.7 mAs) | | | |
| MAE: 32.17 | MAE: 27.64 | MAE: 25.55 | MAE: 24.08 | MAE: 22.06 | MAE: 20.74 |
| SNR: 27.12 | SNR: 28.65 | SNR: 29:48 | SNR: 30.08 | SNR: 30.94 | SNR: 31.52 |
| SSIM: 0.84 | SSIM: 0.87 | SSIM: 0.88 | SSIM: 0.89 | SSIM: 0.91 | SSIM: 0.91 |
| | | Ld2Ld training at half-dose level (15.0~50.7 mAs) | | | |
| MAE: 31.44 | MAE: 27.49 | MAE: 25.54 | MAE: 24.15 | MAE: 22.16 | MAE: 20.82 |
| SNR: 27.26 | SNR: 28.68 | SNR: 29.46 | SNR: 30.03 | SNR: 30.88 | SNR: 31.48 |
| SSIM: 0.84 | SSIM: 0.87 | SSIM: 1.88 | SSIM: 0.89 | SSIM: 0.90 | SSIM: 0.91 |
| | | Ld2Ld training at normal-dose level (30.0~101.4 mAs) | | | |
| MAE: 46.12 | MAE: 28.76 | MAE: 25.77 | MAE: 24.21 | MAE: 22.09 | MAE: 20.50 |
| SNR: 24.53 | SNR: 28.41 | SNR: 29.40 | SNR: 30.00 | SNR: 30.91 | SNR: 31.61 |
| SSIM: 0.74 | SSIM: 0.86 | SSIM: 0.88 | SSIM: 0.89 | SSIM: 0.91 | SSIM: 0.92 |
| | | Ld2Hd training at half-dose level (15.0~50.7 mAs) | | | |
| MAE: 31.07 | MAE: 27.34 | MAE: 25.43 | MAE: 24.03 | MAE: 22.00 | MAE: 20.66 |
| SNR: 27.36 | SNR: 28.73 | SNR: 29.52 | SNR: 30.10 | SNR: 30.96 | SNR: 31.55 |
| SSIM: 0.84 | SSIM: 0.87 | SSIM: 0.88: | SSIM: 0.89 | SSIM: 0.91 | SSIM: 0.91 |
| | | Ld2Hd training at normal-dose level (30.0~101.4 mAs) | | | |
| MAE: 38.08 | MAE: 28.44 | MAE: 25.73 | MAE: 24.18 | MAE: 22.09 | MAE: 20.50 |
| SNR: 25.87 | SNR: 28.45 | SNR: 29.39 | SNR: 30.00 | SNR: 30.90 | SNR: 31.61 |
| SSIM: 0.80 | SSIM: 0.86 | SSIM: 0.88 | SSIM: 0.89 | SSIM: 0.91 | SSIM: 0.92 |

Figure 7:
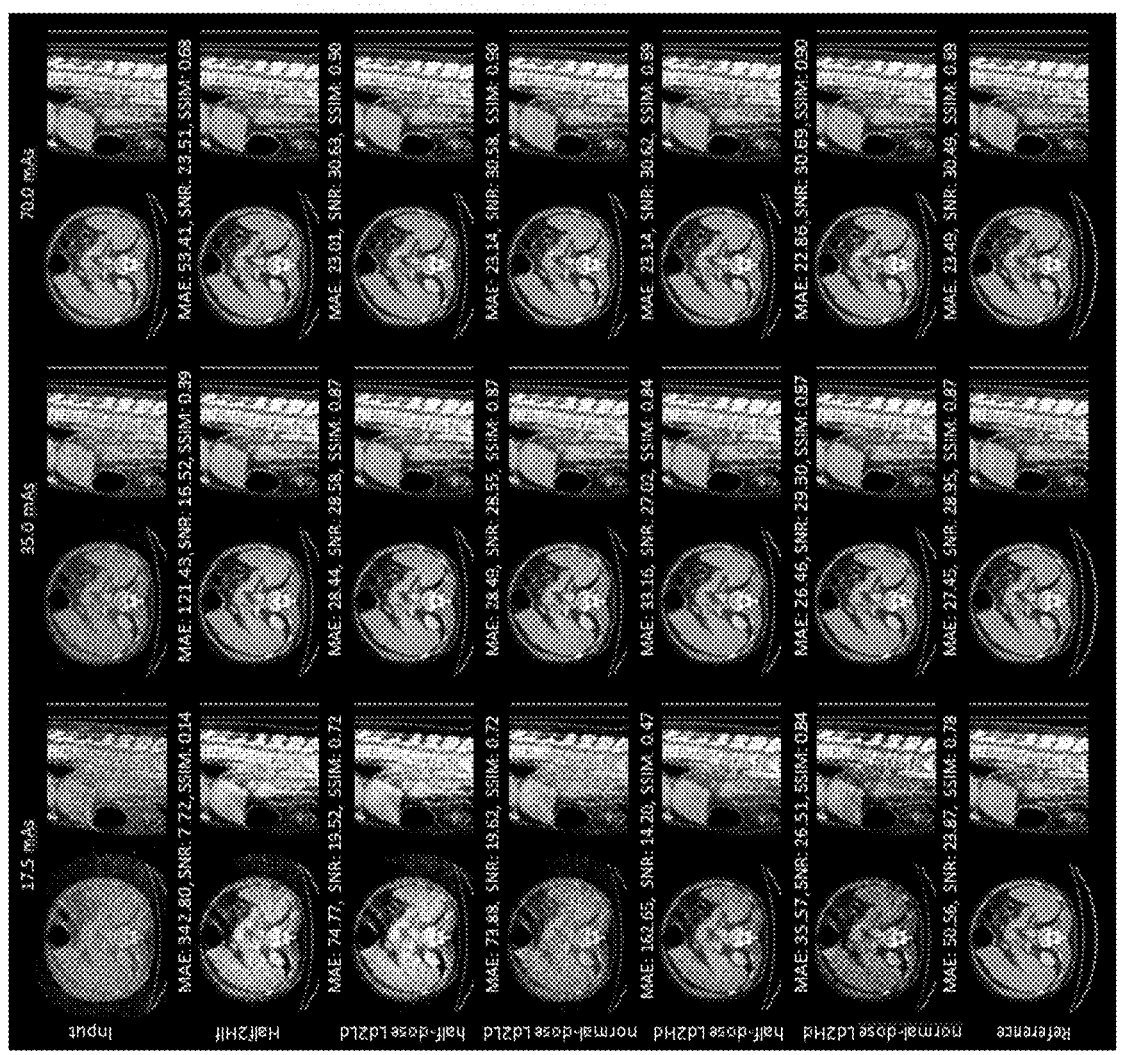
FIG. 7 is a series of images representing image-domain denoised results of simulated test data.

Alternatively, image-domain denoising can be used. Image-domain network denoised images are shown in the FIG. 7. The display windows are the same as those used in FIG. 6. The trend is similar to the count-domain results. Except at the lowest dose level (17.5 mAs), all the methods suppressed noise and removed streaky artifacts. In all cases, the Half2Half denoised images are very similar to those obtained by Ld2Ld training. At 17.5 mAs dose level, only the Ld2Hd at half-dose level was able to remove noise effectively.

The MAE, SNR, and SSIM of the complete test dataset are listed in the Table 4. Although Ld2Ld and Ld2Hd training at half-dose level got better results at almost all dose levels than Half2Half training, the differences are very small. Comparing with the results of the Ld2Ld and Ld2Hd training at normal-dose level, the same trend held true as with count-domain training. Except for the test data at two highest dose levels, Half2Half training got better MAE, SNR and SSIM.

TABLE 4

Quantitative comparison of different image-domain denoising networks on simulated test dataset. (Bold face texts denote the best scores in each column.)

| 17.5 mAs | 35.0 mAs | 52.5 mAs | 70.0 mAs | 105.0 mAs | 140.0 mAs |
|---|---|---|---|---|---|
| Input | | | | | |
| MAE: 342.80 | MAE: 121.43 | MAE: 70.20 | MAE: 53.41 | MAE: 39.51 | MAE: 32.65 |
| SNR: 7.72 | SNR: 13.52 | SNR: 21.16 | SNR: 23.51 | SNR: 26.11 | SNR: 27.75 |
| SSIM: 0.14 | SSIM: 0.39 | SSIM: 0.49 | SSIM: 0.68 | SSIM: 0.78 | SIM: 0.83 |
| Half2Half training (15.0~50.7 mAs) | | | | | |
| MAE: 74.77 | MAE: 28.44 | MAE: 24.57 | MAE: 23.01 | MAE: 21.48 | MAE: 20.73 |
| SNR: 19.52 | SNR: 28.58 | SNR: 30.03 | SNR: 30.63 | SNR: 31.25 | SNR: 31.56 |
| SSIM: 0.72 | SSIM: 0.87 | SSIM: 0.89 | SSIM: 0.90 | SSIM: 0.91 | SSIM: 0.91 |
| Ld2Ld training at half-dose level (15.0~50.7 mAs) | | | | | |
| MAE: 73.88 | MAE: 28:49 | MAE: 24.69 | MAE: 23.14 | MAE: 21.59 | MAE: 20.80 |
| SNR: 19.62 | SNR: 28.55 | SNR: 29.98 | SNR: 30.58 | SNR: 31.20 | SNR: 31.53 |
| SSIM: 0.72 | SSIM: 0.87 | SSIM: 0.89 | SSIM: 0.90 | SSIM: 0.91 | SSIM: 0.91 |
| Ld2Ld training at normal-dose level (30.0~101.4 mAs) | | | | | |
| MAE: 162.65 | MAE: 33.16 | MAE: 25.02 | MAE: 23.14 | MAE: 21.06 | MAE: 19.68 |
| SNR: 14.20 | SNR: 27.02 | SNR: 29.88 | SNR: 30.62 | SNR: 31.47 | SNR: 32.06 |
| SSIM: 0.47 | SSIM: 0.84 | SSIM: 0.88 | SSIM: 0.89 | SSIM: 0.91 | SSIM: 0.92 |
| Ld2Hd training at half-dose level (15.0~50.7 mAs) | | | | | |
| MAE: 35.57 | MAE: 26.46 | MAE: 24.25 | MAE: 22.86 | MAE: 21.42 | MAE: 20.73 |
| SNR: 26.51 | SNR: 29.30 | SNR: 30.16 | SNR: 30.69 | SNR: 31.27 | SNR: 31.56 |
| SSIM: 0.84 | SSIM: 0.87 | SSIM: 0.89 | SSIM: 0.90 | SSIM: 0.91 | SSIM: 0.92 |
| Ld2Hd training at normal-dose level (30.0~101.4 mAs) | | | | | |
| MAE: 50.56 | MAE: 27.45 | MAE: 24.75 | MAE: 23.49 | MAE: 21.29 | MAE: 19.66 |
| SNR: 23.87 | SNR: 28.95 | SNR: 29.98 | SNR: 30.49 | SNR: 31.38 | SNR: 32.08 |
| SSIM: 0.78 | SSIM: 0.87 | SSIM: 0.88 | SSIM: 0.89 | SSIM: 0.91 | SSIM: 0.92 |

Figure 8:
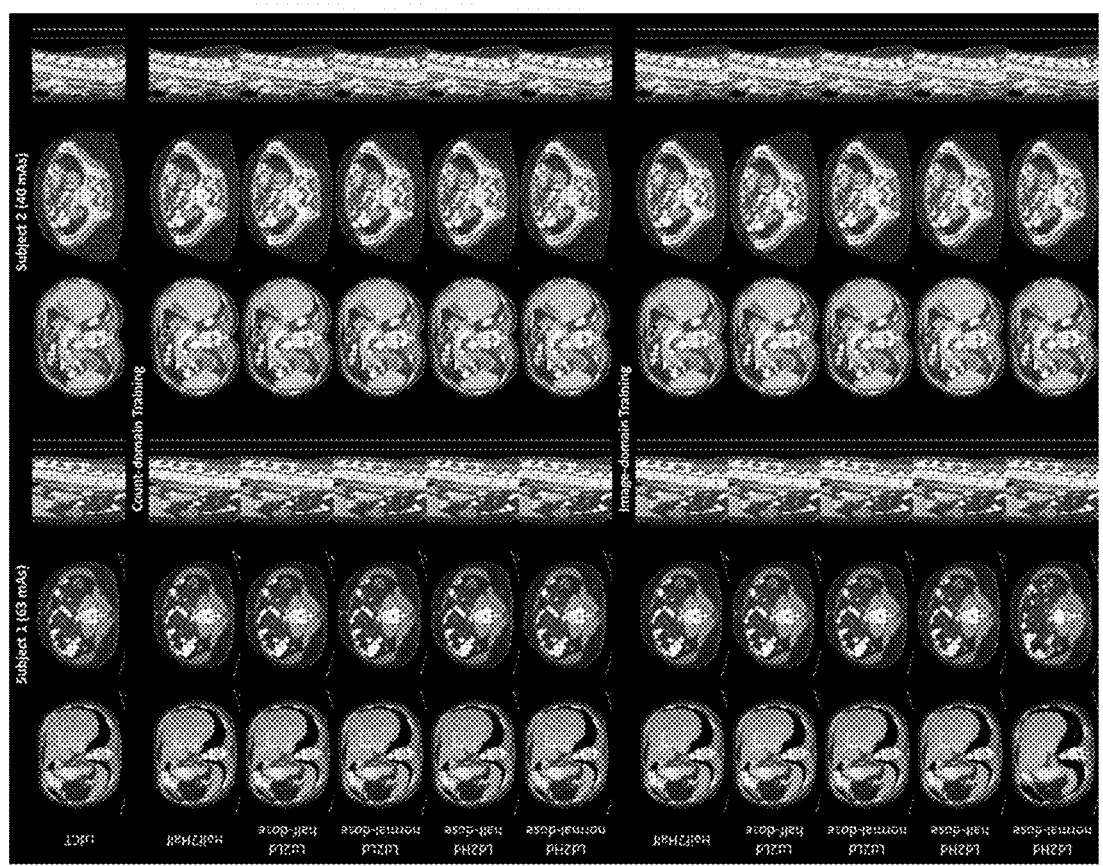
FIG. 8 is a series of images representing denoised results of the real low-dose test data.

The network trained on the simulation data was applied to two real LdCT scans acquired at 40 mAs and 63 mAs and 120 kVp. Representative slices (two transaxial slices and one sagittal slice) and shown in FIG. 8. The display windows are the same as those used in FIG. 6. All the methods generated cleaner images than the inputs. In both count domain and image domain, the proposed Half2Half method produced very similar images and textures to the Ld2Ld and Ld2Hd training.

Deep neural networks have been widely applied in LdCT denoising and produced promising results, but they are hampered by the requirement of high-dose reference data for training. To overcome this limitation, the disclosed method generates both the training input and label from the existing data and thereby eliminates the need for a high-dose reference. The disclosed splitting process splits the measurement in each detector pixel into "n" independent measurements, where n is 2 or greater. Gaussian noise is restored in the split datasets so that the distribution of n split datasets matches that of real CT data (e.g., acquired at 1/n dose levels). The split data were used to train networks using the Noise2Noise training.

By including CT data at a range of dose levels in the training data, the robustness of the neural networks is enhanced and the trained neural networks can be used to remove noise in existing CT images and to improve the CT image quality. Comparing with other supervised training methods, this method allows the large existing datasets to be used to generate training dataset to further improve the neural network performance for CT image denoising. This method can be applied to advanced deep learning techniques to improve the quality of LdCT in clinic.

The network structure used in this study is a modified U-net structure, which includes only two downsampling and two up-sampling paths. The structure of the network can be changed to any other supervised networks that may have better performance on a specific task, including, but not limited to, convolution neural networks (Chen et al, Low-Dose CT With a Residual Encoder-Decoder Convolutional Neural Network, IEEE Trans Med Imaging, DOI: 10.1109/TMI.2017.2715284), stacked networks (Du et al, Stacked competitive networks for noise reduction in low-dose CT, PLOS One, https://doi.org/10.1371/journal.pone.0190069), and network with quadratic neurons (Fan et al, Quadratic Autoencoder for low-dose CT denoising, IEEE Trans Medical Imaging, DOI: 10.1109/TMI.2019.2963248). The system further includes a loss function that should meet the requirements of Noise2Noise training, such as mean squared error, mean absolute error, or combination of them. (See, e.g., [Lehtinen 2018]: (Lehtinen J, Munkberg J, Hasselgren J, Laine S, Karras T, Aittala M and Aila T 2018 Noise2noise: Learning image restoration without clean data *arXiv Prepr. arXiv*1803.04189). The loss function can also be combined with perceptual loss and other feature extractors, such as edge detection (Gholizadeh-Ansari, M., Alirezaie, J. & Babyn, P. Deep Learning for Low-Dose CT Denoising Using Perceptual Loss and Edge Detection Layer. J Digit Imaging 33, 504-515 (2020). https://doi.org/10.1007/s10278-019-00274-4). Generative adversarial networks (GANs) are considered sub-optimal as the adversarial networks could be seen as a trainable loss function and GANs will try to predict the noise- or artifact-like textures and structures. See, e.g., [Liang 2019]: (Liang X, Chen L, Nguyen D, Zhou Z, Gu X, Yang M, Wang J and Jiang S 2019 Generating synthesized computed tomography (CT) from cone-beam computed tomography (CBCT) using Cycle-GAN for adaptive radiation therapy *Phys. Med. Biol.* 64 125002).

Figure 9:
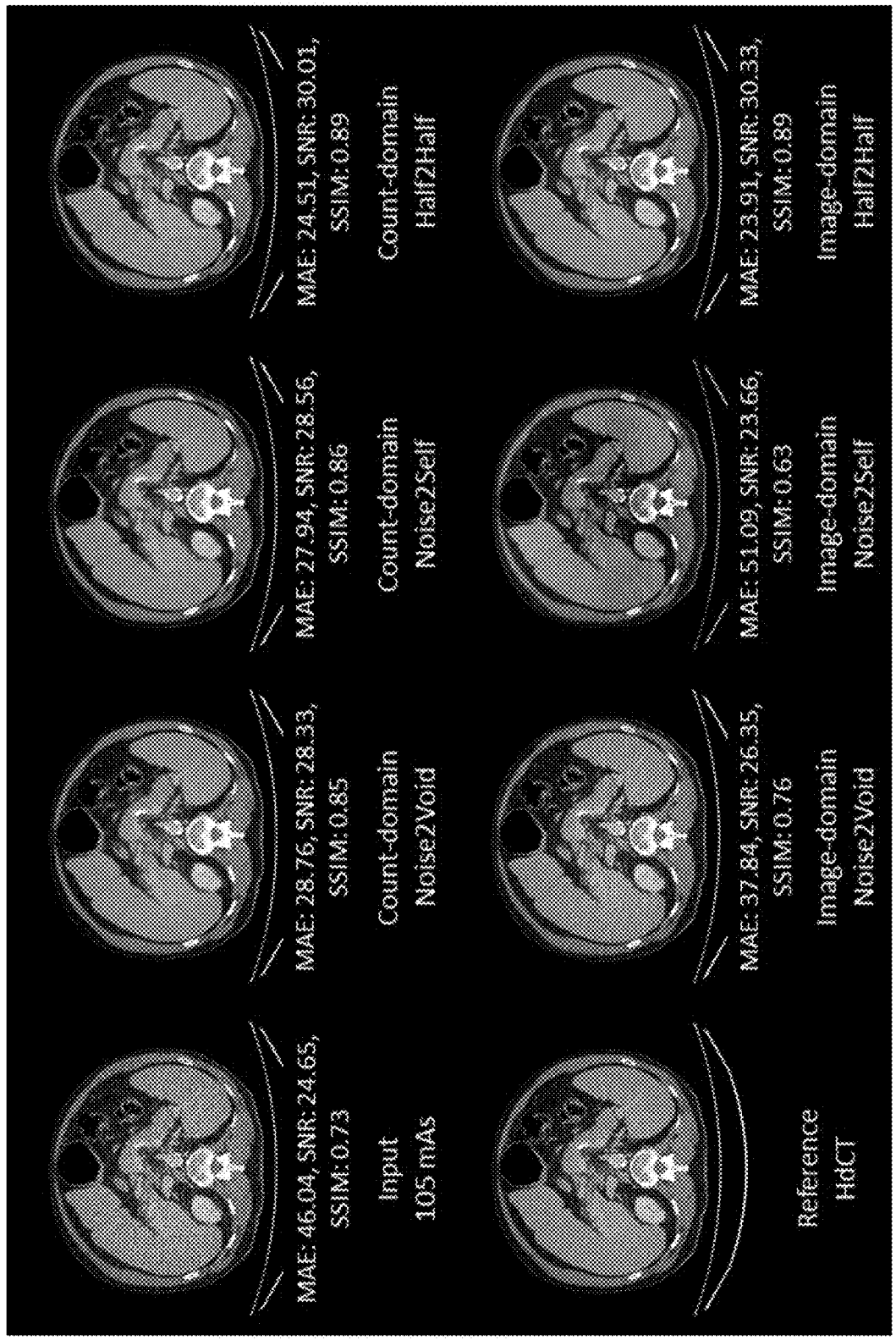
FIG. 9 is a series of images representing denoised results using other denoising techniques referred to as Noise2Void and Noise2Self.

The data requirement of the proposed method is the same as self-supervised or unsupervised training because no other independent data is used as reference. Two Noise2Noise based self-supervised methods (Noise2Void and Noise2Self) have been proposed recently, but are limited to removing spatially independent noise. See, e.g., [Krull 2019]: (Krull A; Buchholz, T-O; and Jug, F; 2019, Noise2Void—Learning Denoising From Single Noisy Images *The IEEE Conference on Computer Vision and Pattern Recognition* (*CVPR*)) and [Batson/Royer 2019]: (Batson, J and Royer, L; 2019, Noise2self; Blind denoising by self-supervision *arXiv Prepr. arXiv*1901.11365). Streaky artifacts in CT images have long-range correlation and cannot be removed by these two methods. To demonstrate this, Noise2Void and Noise2Self denoising networks were applied to the simulation data described herein, and the results of the test data are shown in the FIG. 9. The MAE, SNR and SSIM of each image are listed at the bottom of each panel. The display windows are the same as those used in FIG. 6. While these two methods could suppress the noise in the count domain, the resultant images were blurrier than the Half2Half results and the image quality was also worse in terms of MAE, SNR and SSIM. In the image domain, neither Noise2Void nor Noise2Self could suppress the streaky artifacts. In comparison, the method described herein can restore more details in the count-domain denoising and removed streaky artifacts in the image-domain denoising.

Figure 10:
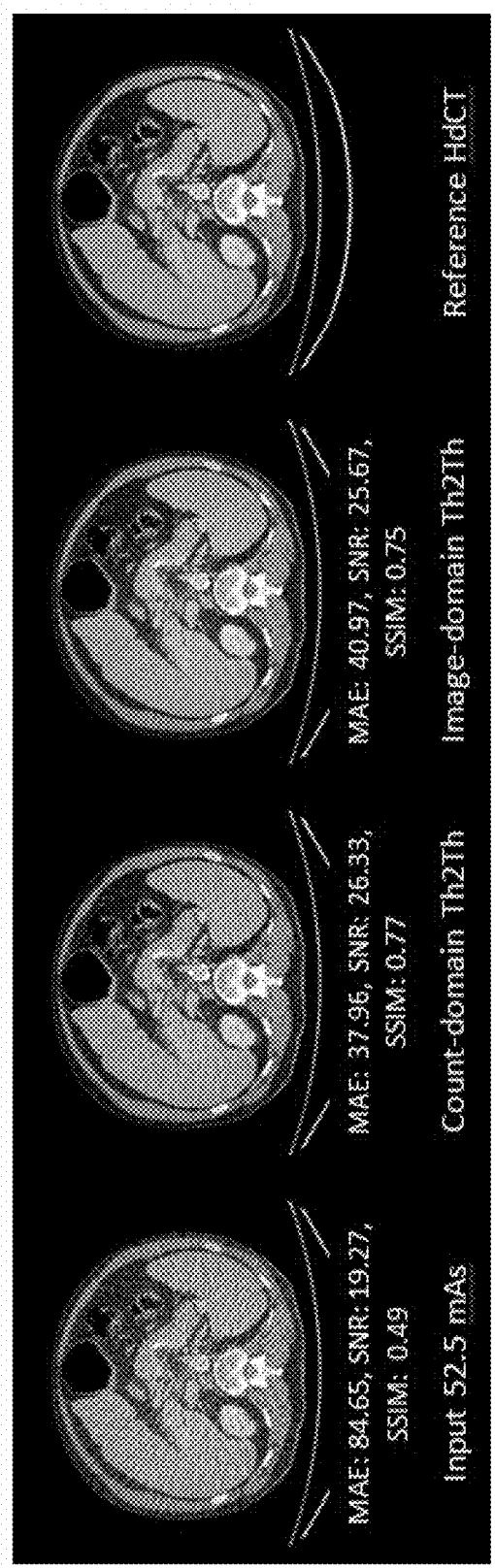
FIG. 10 is a series of images representing denoised results using a technique referred to as Th2Th.

As noted above, the original full-dose scan is split into multiple partial-dose scans that are to be independent datasets. As shown in FIG. 1, the training labels were generated using the model in (3)-(6). Thus, when using a half-dose scan, the second dataset is generated using the remaining events to avoid any correlation between the two half-dose scans. If the binomial thinning process is used to generate both half-dose scans and use one thinning dataset as the training input and the other thinning dataset as the training label (Th2Th model), there would be high correlation between the input and label, which violated that assumption of Noise2Noise training. Table 5 compares the correlation coefficient of the Half2Half and Th2Th datasets. As expected the Th2Th data have a correlation efficient close to 0.5. The same network was trained using Th2Th training, and the denoised image is shown in the FIG. 10. Comparing with the Half2Half results in FIG. 6 and FIG. 7, the results of Th2Th trained networks were much noisier (e.g., 3.2-4.3 dB reduction in PSNR) than those of Half2Half trained networks because correlated noise in the Th2Th dataset were not removed in the training process.

TABLE 5

Noise cross-correlation coefficient between training data and label of the Half2Half and Th2Th.

| | Simulated Dose Level | Cross-Correlation Coefficient Between Half2Half Pairs | Cross-Correlation Coefficient Between Th2Th Pairs |
|---|---|---|---|
| Subject 1 | 15.9 mAs | $6.31 \times 10^{-4}$ | $4.82 \times 10^{-1}$ |
| | 31.8 mAs | $5.07 \times 10^{-4}$ | $4.91 \times 10^{-1}$ |
| | 47.7 mAs | $4.85 \times 10^{-4}$ | $4.94 \times 10^{-1}$ |
| | 15.0 mAs | $4.10 \times 10^{-4}$ | $4.81 \times 10^{-1}$ |
| Subject 2 | 30.0 mAs | $4.38 \times 10^{-4}$ | $4.90 \times 10^{-1}$ |
| | 45.0 mAs | $3.05 \times 10^{-4}$ | $4.94 \times 10^{-1}$ |
| | 16.9 mAs | $4.61 \times 10^{-4}$ | $4.78 \times 10^{-1}$ |
| Subject 3 | 3.8 mAs | $2.27 \times 10^{-4}$ | $4.88 \times 10^{-1}$ |
| | 50.7 mAs | $4.10 \times 10^{-4}$ | $4.89 \times 10^{-1}$ |

Thus, a Half2Half method can be used to train an LdCT denoising network without requiring high-dose CT scans or repeated scans of the same subject. This allows a large existing dataset to be used to improve the network performance. The method is expected to facilitate the application of advanced deep learning techniques to improve the quality of LdCT in clinic.

The method and system described herein can be implemented in a number of technologies but generally relate to processing circuitry for performing the denoising described herein. In one embodiment, the processing circuitry is implemented as one of or as a combination of: an application specific integrated circuit (ASIC), a filed programmable gate array (FPGA), a generic array of logic (GAL), a programmable array of logic (PAL), circuitry for allowing one-time programmability of logic gates (e.g., using fuses) or reprogrammable logic gates. Furthermore, the processing circuitry can include a computer processor and having embedded and/or external non-volatile computer readable memory (e.g., RAM, SRAM, FRAM, PROM, EPROM, and/or EEPROM) that stores computer instructions (binary executable instructions and/or interpreted computer instructions) for controlling the computer processor to perform the processes described herein. The computer processor circuitry may implement a single processor or multiprocessors, each supporting a single thread or multiple threads and each having a single core or multiple cores. In an embodiment in which neural networks are used, the processing circuitry used to train the artificial neural network need not be the same as the processing circuitry used to implement the trained artificial neural network that performs the denoising described herein. For example, processor circuitry and memory may be used to produce a trained artificial neural network (e.g., as defined by its interconnections and weights), and an FPGA may be used to implement the trained artificial neural network. Moreover, the training and use of a trained artificial neural network may use a serial implementation or a parallel implementation for increased performance (e.g., by implementing the trained neural network on a parallel processor architecture such as a graphics processor architecture).

Figure 11:
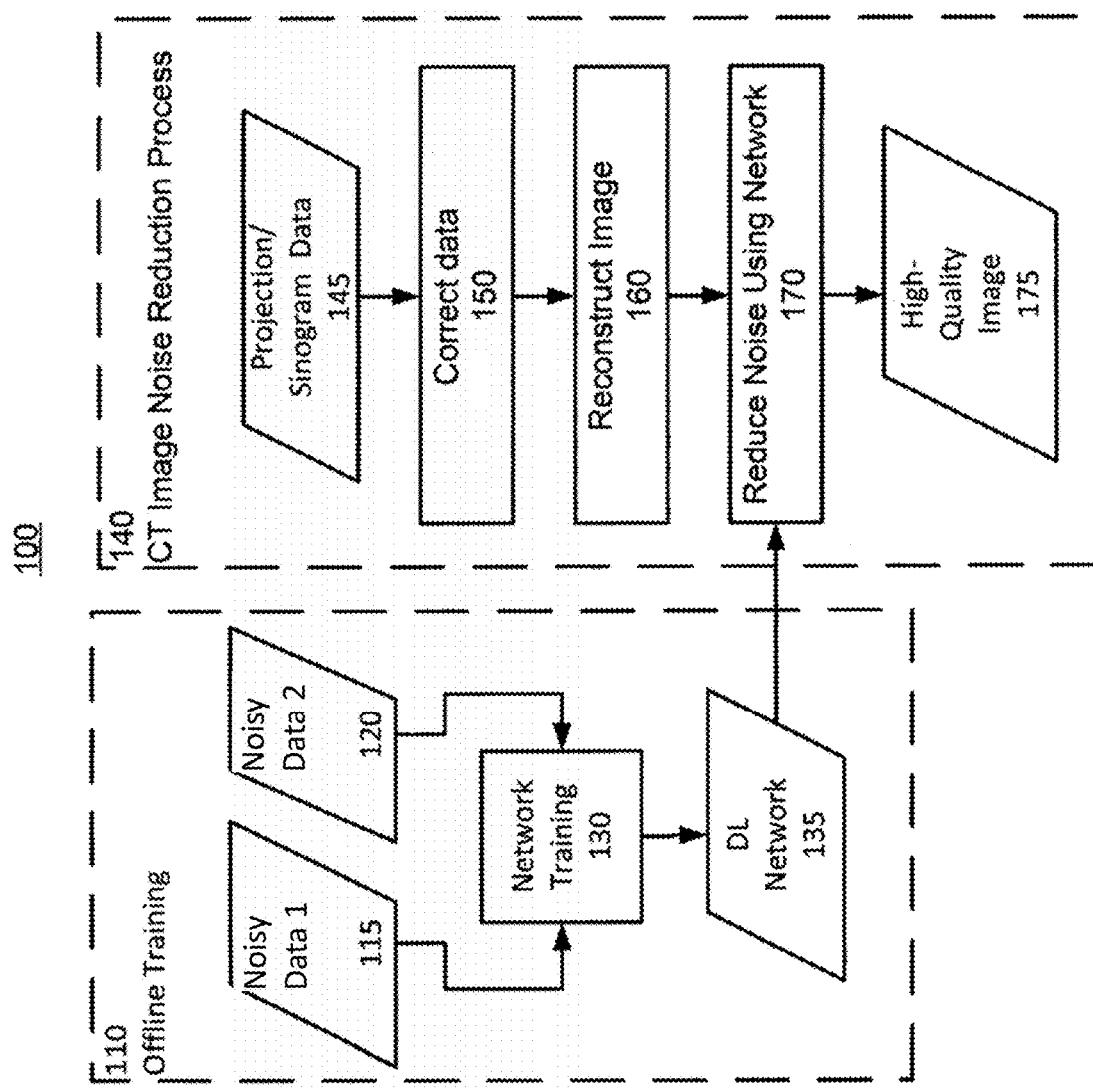
FIG. 11 shows an example of a flow diagram of a method for reducing noise that uses a deep-learning (DL) network to process a reconstructed image, according to one implementation.

FIG. 11 shows a flow diagram of method 100, which has two processes: (a) process 110 for offline training, corresponding to the image-domain training process described above, and (b) process 140 for reconstructing a high-quality CT image from projection data (which can also be referred to as a sinogram).

The process 110 of method 100 performs offline training of the deep learning (DL) network 135. In step 130 of process 110, a first set of noisy data 115 and a first set of noisy data 120 are used as training data to train a DL network, resulting in the DL network being output from step 130. In an example using reconstructed images for data 115 and 120, the offline DL training process 110 trains the DL network 135 using a large number of noisy reconstructed images 115/120 to train the DL network 135 to produce images with the noise reduced, using the above described image-domain N2N training method.

In process 140 of method 100, the projection data 145 (also referred to as scan data or sinogram data) is corrected in step 150, and then, it step 160, a CT image is reconstructed from the corrected projection data using an image reconstruction process (e.g., an inverse Radon transformation).

In step 150, the projection data can be corrected for a detector offset (e.g., due to dark current or noise), pile up, variations in quantum efficiency in the detectors (e.g., between detector elements and as a function of energy of the X-ray photons), etc. Further, these corrections can be based on calibration data, empirical, and known parameters (e.g., the geometry of the scanner, the detector elements, anti-scatter grids, etc.).

In step 160, the image reconstruction can be performed using a back-projection method, a filtered back-projection method, a Fourier-transform-based image reconstruction method, an iterative image reconstruction method (e.g., algebraic reconstruction technique), a matrix-inversion image reconstruction method, or a statistical image reconstruction method.

In step 170, the reconstructed image is denoised using the DL network 135. The result of which is a high-quality image 175. Thus, noisy CT images resulting from the CT reconstruction in step 160 can be processed using DL denoising technique applying the network generated by the offline DL training process 110.

Figure 12:
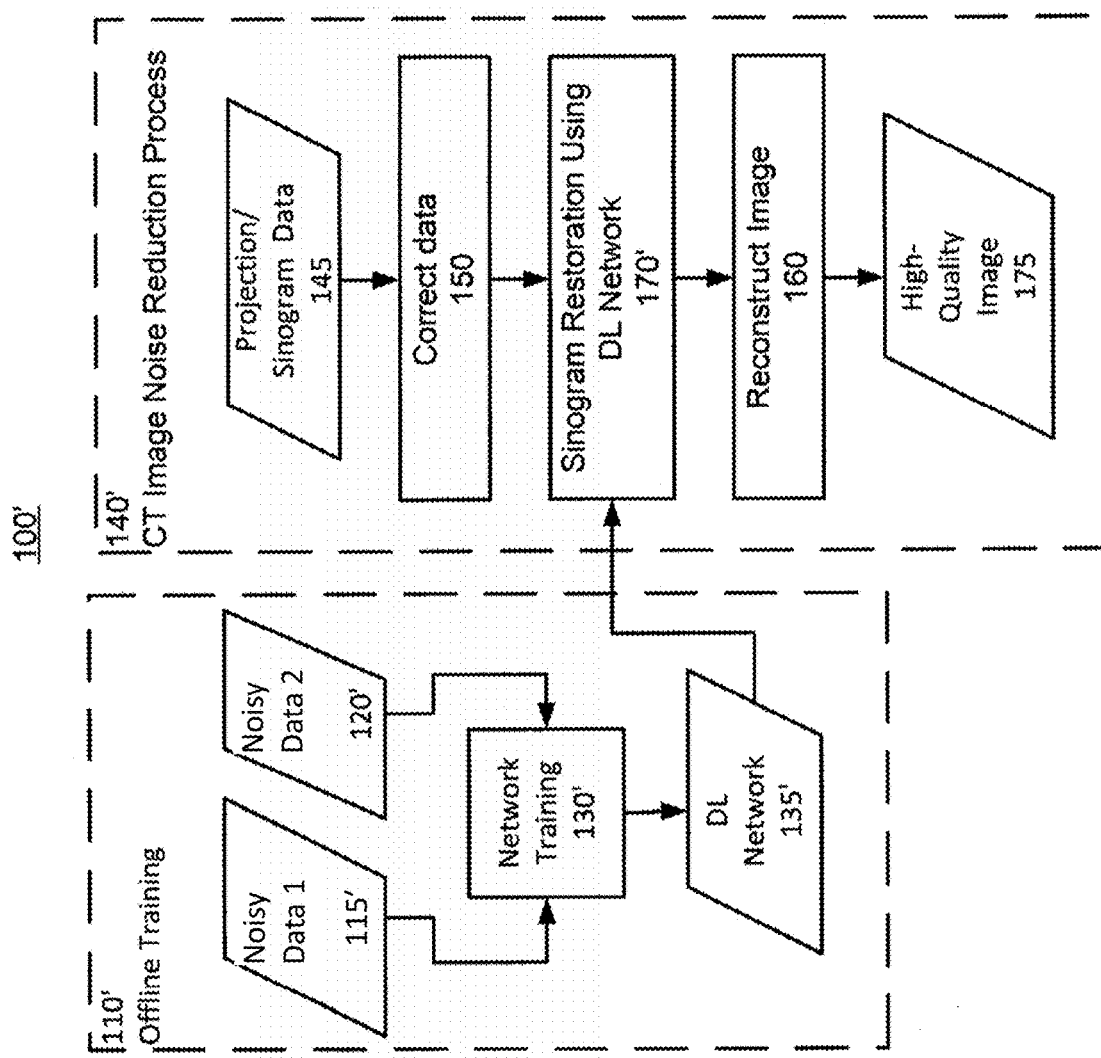
FIG. 12 shows an example of a flow diagram of a method for reducing noise that uses a DL network to process sinogram data, according to one implementation.

FIG. 12 shows an alternative method 100' as compared to method 100. In method 100', the DL network 135' is applied in step 170' to restoring the sinogram before the image reconstruction step 160, rather than denoising the reconstructed image after the image reconstruction step 160. In this case the DL network 135' represents a network that has been trained at step 130' of process 110' using a large number of noisy sinograms 115' that are paired with corresponding noisy sinograms 120'. The DL network 135' is trained by the above-described count-domain N2N method with reference to FIGS. 1 and 2. For example, in step 140', raw data 145 (e.g., pre-log) can be processed by pre-log corrections and converted to sinogram data in step 150. Then, in the sinogram restoration step 170' and the reconstruction step 160, the DL network 135' is applied to sinogram restoration, and, after sinogram correction, image reconstructions are applied to generate the high-quality image 175.

In certain implementations a DL network 135' can be used to restore a sinogram and a DL network 135 can be used to denoise the image reconstructed from the restored sinogram within a single method 100 to generate the high-quality image 175.

Figure 13:
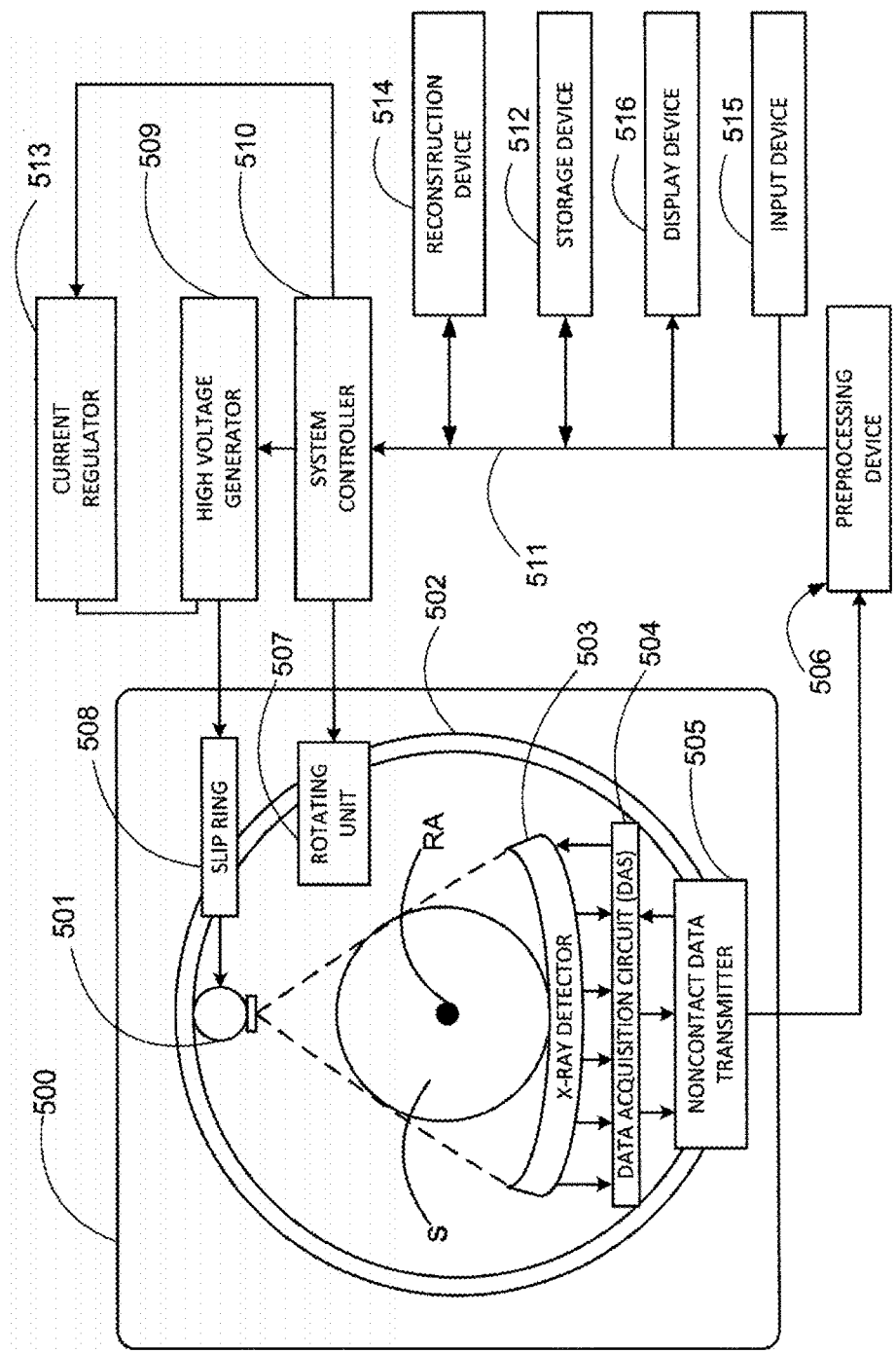
FIG. 13 shows a schematic of an implementation of a computed tomography (CT) scanner, according to one implementation.

FIG. 13 illustrates an implementation of the radiography gantry included in a CT apparatus or scanner. The CT apparatus or CT scanner can be used to acquire count-domain projections or sinograms, and these can be used as the noisy sinograms 115' or 120' the sinogram data 145. The sinogram can also be used to reconstruct CT images, which can be used as the noisy data 115 or 120.

As shown in FIG. 13, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted on the annular frame 502 across an object (e.g., a patient labeled St). The annular frame 502 is rotatably supported around a rotation axis RA. A rotating unit 507 rotates the annular frame 502 at a high speed, such as 0.4 sec/rotation, while the object is being moved along the axis RA into or out of the illustrated page.

Further details of an X-ray computed tomography (CT) apparatus are described below with reference to FIG. 13. As used herein, X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The techniques and structures herein can be applied to either type. In this case, the rotate/rotate type, which is currently the mainstream, will be accentuated.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object, whose cross-sectional area is represented by a circle. For example, the X-ray tube 501 having an average X-ray energy during a first scan can be less than an average X-ray energy during a second scan. In this case two or more scans can be obtained corresponding to different X-ray energies. The X-ray detector 503 is located at an opposite side from the X-ray tube 501 across the object for detecting the emitted X-rays that have transmitted through the object. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal. The X-ray detector 503 and the DAS 504 are configured to handle a predetermined total number of projections per rotation (TPPR).

The above-described data is sent to a preprocessing device 506, which is housed in a console outside the radiography gantry 500 through a non-contact data transmitter 505. The preprocessing device 506 performs certain corrections, such as sensitivity correction on the raw data. A storage device 512 (e.g., a memory or non-volatile storage hardware, such as a magnetic hard drive and/or a solid state drive) stores the resultant data, which is also called projection data at a stage immediately before reconstruction processing. The storage device 512 is connected to a system controller 510 through a data control bus 511, together with a reconstruction device 514, input device 515, and display 516. The system controller 510 controls a current regulator 513 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 501 and the X-ray detector 503 are diametrically mounted on the annular frame 502 and are rotated around the object as the annular frame 502 is rotated about the rotation axis RA. In the fourth-generation geometry system, the detectors are fixedly placed around the patient and an X-ray tube rotates around the patient. In an alternative embodiment, the radiography gantry 500 has multiple detectors arranged on the annular frame 502, which is supported by a C-arm and a stand.

The storage device 512 can store the measurement value representative of the irradiance of the X-rays at the X-ray detector unit 503. Further, the storage device 512 can store a dedicated program for executing various steps of method 100 and/or method 100' for correcting low-count data and CT image reconstruction.

The reconstruction device 514 can execute various steps of method 100 and/or method 100'. Further, reconstruction device 514 can execute pre-reconstruction processing image processing such as volume rendering processing and image difference processing as needed.

The pre-reconstruction processing of the projection data performed by the preprocessing device 506 can include correcting for detector calibrations, detector nonlinearities, and polar effects, for example. Further, the pre-reconstruction processing can include various steps of method 100 and/or method 100'.

Post-reconstruction processing performed by the reconstruction device 514 can include filtering and smoothing the image, volume rendering processing, and image difference processing as needed. The image reconstruction process can implement various steps of method 100 and/or method 100' in addition to various CT image reconstruction methods. The reconstruction device 514 can use the storage device 512 to store, e.g., projection data, reconstructed images, calibration data and parameters, and computer programs.

The reconstruction device 514 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the storage device 512 can be non-volatile, such as ROM, EPROM, EEPROM or FLASH memory. The storage device 512 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 514 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a given processor and a given operating system or any operating systems known to those skilled in the art. Further, CPU can be implemented as multiple processors cooperatively working in parallel to perform the instructions.

In one implementation, the reconstructed images can be displayed on a display 516. The display 516 can be an LCD display, CRT display, plasma display, OLED, LED or any other display known in the art.

The storage device 512 can be a hard disk drive, CD-ROM drive, DVD drive, FLASH drive, RAM, ROM or any other electronic storage known in the art.

As discussed above, methods 100 and 100' can also be used with magnetic resonance imaging (MRI) data. The exemplary implementation of MRI scanner is now provided.

Figure 14:
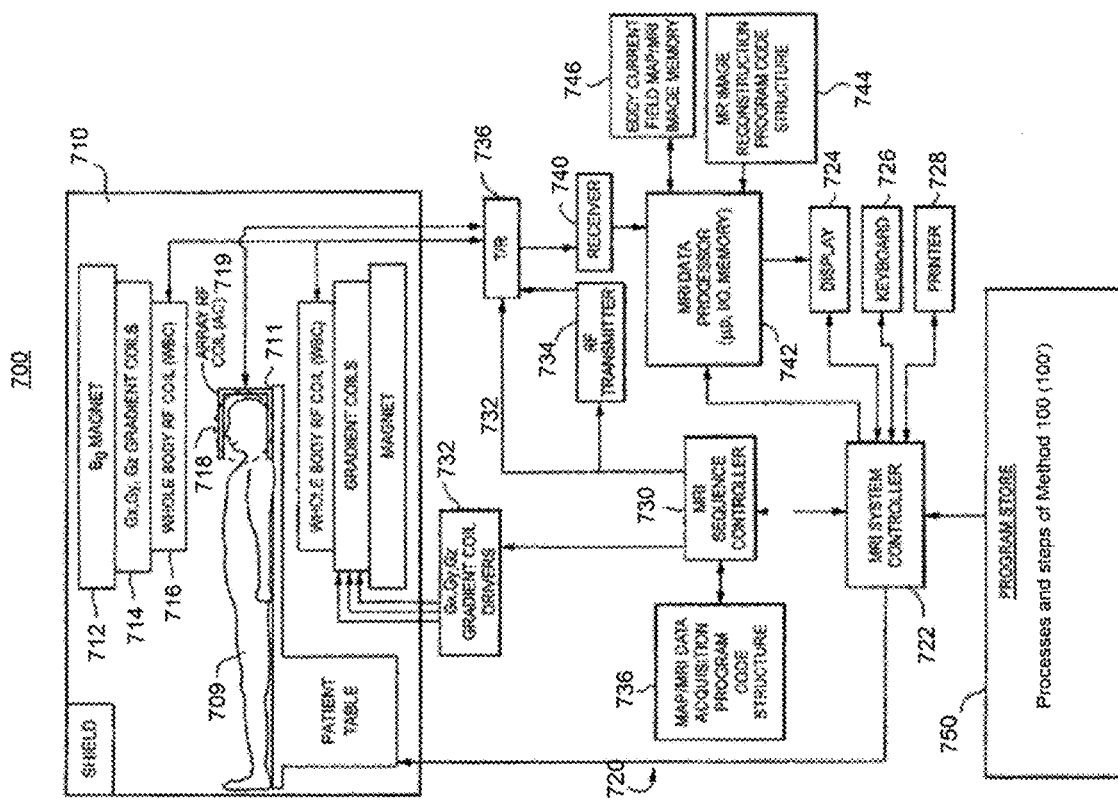
FIG. 14 shows a schematic of an implementation of a magnetic resonance imaging (MRI) scanner, according to one implementation.

Method 100 (100') can also be implemented using MRI data acquired using an MRI scanner such as the non-limiting example of the MRI scanner 700 shown in FIG. 14. MRI is an imaging scan method that magnetically excites nuclear spins of a subject placed in a magnetostatic field by a radio frequency (RF) pulse having a Larmor frequency thereof, to generate an image from magnetic resonance signal data generated with the excitation.

The MRI scanner 700 acquires k-space data (or scan data) of an object to be imaged, by the RF receiving coil, and the k-space data is used by the MRI data processor to reconstruct MR images. The k-space data can be used as the noisy data 115' or 120', or the scan data 145. The reconstructed MR images can be used as the noisy data 115 or 120.

FIG. 14 illustrates a non-limiting example of an exemplary overview of a magnetic resonance imaging (MRI) system 700 according to one or more aspects of the disclosed subject matter. The MRI system 700 includes a gantry 710 (shown in schematic cross section) and various related system components interfaced therewith. At least the gantry 710 is typically located in a shielded room. One MRI system geometry depicted in FIG. 14 includes a substantially coaxial cylindrical arrangement of the static field $B_0$ magnet 712, a Gx, Gy, and Gz gradient coil set 714 and a large whole-body RF coil (WBC) assembly 716. The physical Gx, Gy, and Gz gradient axes can be controlled in such a way to create $G_{RO}$, $G_{PE}$, and $G_{SS}$ (readout, phase encode, slice-selection) functional axes. Along the horizontal axis of the cylindrical array of elements is an imaging volume 718 shown as substantially encompassing the chest of a patient 709 supported by a patient table 711. A smaller RF coil 719 is shown as more closely coupled to the head of the patient 709 in image volume 718. RF coil 719 can be a surface coil or array or the like, and can be customized or shaped for particular body parts, such as skulls, arms, shoulders, elbows, wrists, knees, legs, chests, spines, etc. An MRI system controller 722 interfaces with MRI sequence controller 730, which, in turn controls the Gx, Gy, and Gz gradient coil drivers 732, as well as the RF transmitter 734 and the transmit/receive switch 736 (if the same RF coil is used for both transmission and reception). The MRI sequence controller 730 includes suitable program code structure 738 for implementing data acquisition sequences including a fast spin echo (FSE) pulse sequence with a time-shifted $G_{SS}$ gradient, for example. The MRI system controller 722 also can optionally interface with a printer 728, a keyboard 726, and a display 724.

The various related system components include an RF receiver 740 providing input to data processor 742, which is configured to create processed image data, which is then sent to display 724. The MRI data processor 742 is also configured for access to previously acquired data acquisitions of pulse sequences with a time-shifted $G_{SS}$ gradient stored in MRI image memory 746, and to perform various steps of method 100 and/or method 100' stored in code structure 750, as well as MRI image reconstruction program code structure 744.

Also illustrated in FIG. 14 is a generalized depiction of an MRI system program store (memory) 750 where program code structures (e.g., to perform various steps of method 100 and/or method 100', for defining graphical user interfaces and accepting operator inputs to the graphical user interface) are stored in non-transitory computer-readable storage media accessible to the various data processing components of the MRI system. The program store 750 may be segmented and directly connected, at least in part, to different elements of the various related system components as needed.

Figure 15:
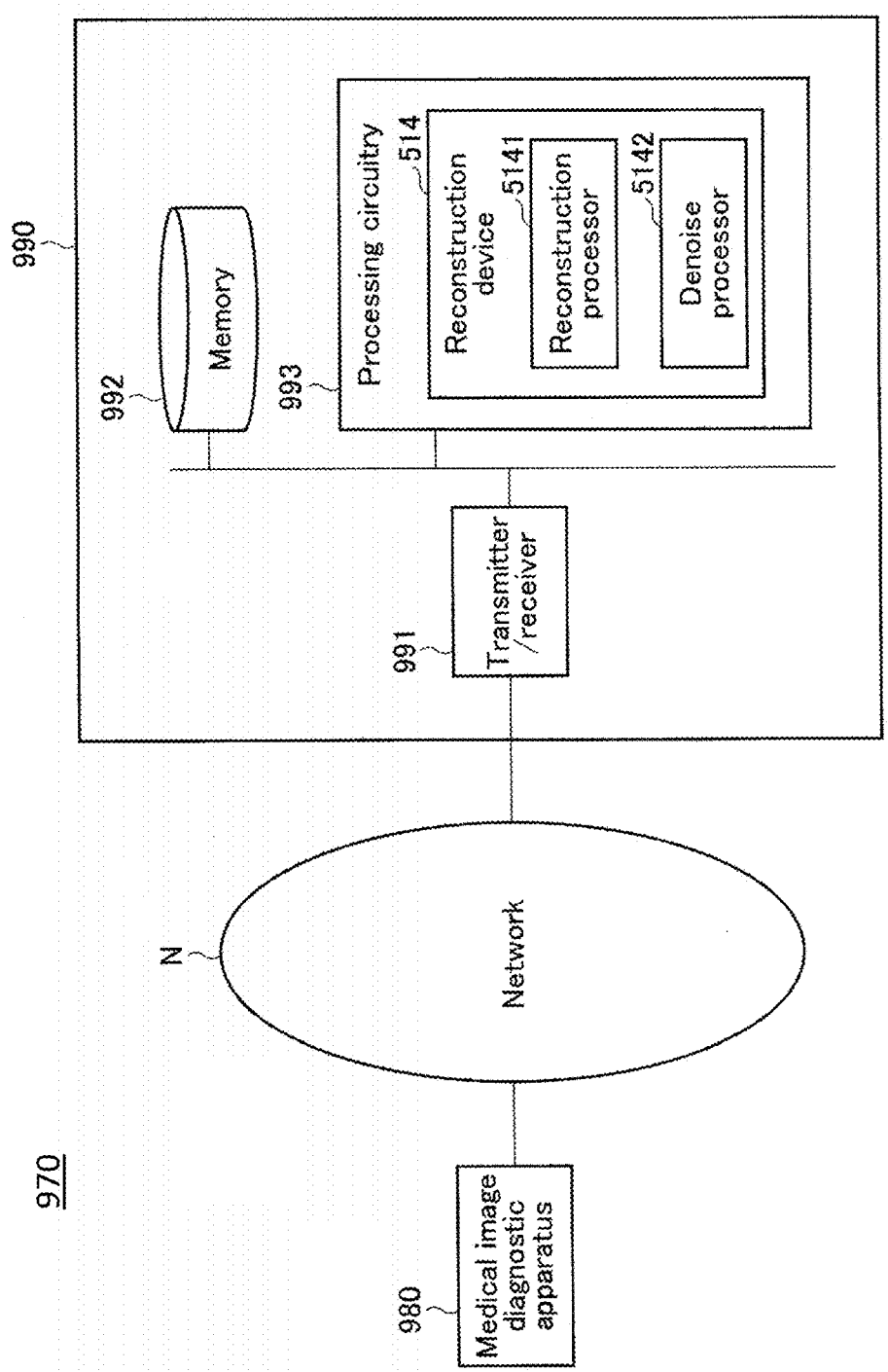
FIG. 15 shows an example of a medical image processing system that has a client-server configuration involving an intermediary network.

FIG. 15 shows an example of a medical image processing system 970 that has a client-server configuration involving an intermediary computer network (N). As shown in FIG. 15, the medical image processing system 970 includes a medical image diagnostic apparatus 980 as a client-side apparatus, and a medical image processing apparatus 990 as a server-side apparatus connected with the medical image diagnostic apparatus 980 via a computer network N.

The medical image diagnostic apparatus 980 may typically be an X-ray CT apparatus as shown in FIG. 13, or an MRI apparatus as shown in FIG. 14.

The medical image processing apparatus 990 includes a transmitter/receiver 991, a storage device 992, and processing circuitry 993. The transmitter/receiver 991 transmits data to, and receives data from, the medical image diagnostic apparatus 980 via the computer network N. The storage device 992 stores information such as medical image data received from the medical image diagnostic apparatus 980, and various dedicated programs for executing the reconstruction processing, denoising processing, etc. as described. The processing circuitry 993 is a programmed processor or other special purpose hardware (e.g., a programmable logic device such as an FPGA) to realize the functions of the reconstruction device 514 as described.

With these configurations, the medical image diagnostic apparatus 980 is not required to implement the functions of the reconstruction device 514. Therefore, the processing load within the medical image diagnostic apparatus 980 as well as the costs associated with the medical image diagnostic apparatus 980 can be reduced. Also, the reconstruction processing and the denoising processing are performed in a uniform manner in the medical image processing apparatus 990 as a server side. Thus, it is possible to avoid variations in image qualities, etc. that might otherwise occur due to differences in operators when the reconstruction processing and the denoising processing are preformed in each local medical image diagnostic apparatus.

In the preceding description, specific details have been set forth, such as a particular method and system for denoising CT images using a neural network and descriptions of various components and processes used therein. It should be understood, however, that techniques herein may be practiced in other embodiments that depart from these specific details, and that such details are for purposes of explanation and not limitation. Embodiments disclosed herein have been described with reference to the accompanying drawings. Similarly, for purposes of explanation, specific numbers, materials, and configurations have been set forth in order to provide a thorough understanding. Nevertheless, embodiments may be practiced without such specific details. Components having substantially the same fictional constructions are denoted by like reference characters, and thus any redundant descriptions may be omitted.

Various techniques have been described as multiple discrete operations to assist in understanding the various embodiments. The order of description should not be construed as to imply that these operations are necessarily order dependent. Indeed, these operations need not be performed in the order of presentation. Operations described may be performed in a different order than the described operations may be omitted in additional embodiments.

Those skilled in the art will also understand that there can be many variations made to the operations of the techniques explained above while still achieving the same objectives of the invention. Such variations are intended to be covered by the scope of this disclosure. As such, the foregoing descriptions of embodiments of the invention are not intended to be limiting. Rather, any limitations to embodiments of the invention are presented in the following claims.

What is claimed:

1. A method of generating an image denoising system, the method comprising:
    acquiring single scan data obtained from a single scan of a subject, the single scan data being count-domain projection data;
    identically distribute the acquired single scan data to generate first and second substantially independent partial scan data, wherein the first partial scan data is generated by applying a thinning model to the projection data and the second partial scan data is generated by subtracting the generated first partial scan data from the projection data; and
    training a machine learning-based system based on the generated first substantially independent, identically distributed, partial scan data as input training data, and the generated second substantially independent, identically distributed, partial scan data as label data to produce a trained machine learning-based system.

2. The method as claimed in claim 1, wherein each of the first and second partial scan data corresponds to a half-dose scan.

3. The method as claimed in claim 1, wherein the machine learning-based system comprises a neural network and the trained machine learning-based system comprises a trained neural network.

4. The method as claimed in claim 3, wherein the neural network comprises a deep neural network.

5. The method as claimed in claim 1, wherein the acquired single scan data includes court-domain projection data.

6. The method as claimed in claim 1, wherein the acquired single scan data includes image-domain reconstructed images.

7. The method as claimed in claim 1, further comprising adding Gaussian noise to at least one of the generated first and second substantially independent, identically distributed, partial scan data prior to the training step.

8. The method of claim 1, wherein the generated first and second substantially independent, identically distributed, partial scan data are first and second nearly independent, identically distributed, partial scan data.

9. The method of claim 1, wherein the generated first and second substantially independent, identically distributed, partial scan data are first and second virtually independent, identically distributed, partial scan data.

10. The method of claim 1, wherein the generated first and second substantially independent identically distributed partial scan data are first and second completely independent, identically distributed, partial scan data.

11. A trained machine learning-based system produced according to the method of claim 1.

12. A system for generating an image demising system, comprising:
    processing circuitry configured to
        acquire single scan data obtained from a single scan of a subject, the single scan data being count-domain projection data;
        identically distribute the acquired single scan data to generate first and second substantially independent partial scan data, wherein the first partial scan data is generated by applying a thinning model to the projection data and the second partial scan data is generated by subtracting the generated first partial scan data from the projection data; and
        train a machine learning-based system based on the generated first substantially independent, identically distributed, partial scan data as input training data, and the generated second substantially independent, identically distributed, partial scan data as label data to produce a trained machine learning-based system.

13. The system as claimed in claim 12, wherein each of the first and second partial scan data corresponds to a half-dose scan.

14. The system as claimed in claim 12, wherein the machine learning-based system comprises a neural network and the trained machine learning-based system comprises a. trained neural network.

15. The system as claimed in claim 14, wherein the neural network comprises a deep neural network.

16. The system as claimed in claim 12, wherein the acquired single scan data includes count-domain projection data.

17. The system as claimed in claim 12, wherein the acquired single scan data includes image-domain reconstructed images.

18. The system as claimed in claim 12, wherein the processing circuitry is further configured to add Gaussian noise to at least one of the generated first and second substantially independent, identically distributed, partial scan data prior to the processing circuitry training the machine learning-based system.

19. The system as claimed in claim 12, wherein the generated first and second substantially independent, identically distributed, partial scan data are first and second completely independent, identically distributed, partial scan data.

20. A trained machine learning-based system produced using the system according to claim 12.

21. A medical image processing apparatus, comprising:
processing circuitry configured to
receive medical image data; and
perform denoising processing by applying the medical image data to a trained machine learning-based system, wherein the trained machine learning-based system is generated by (a) acquiring single scan data obtained from a single scan of a subject, the single scan data being count-domain projection data, (b) identically distributing the acquired single scan data to generate first and second substantially independent partial scan data, wherein the first partial scan data is generated by applying a thinning model to the projection data and the second partial scan data is generated by subtracting the generated first partial scan data from the projection data; and (c) training a machine learning-based system based on the generated first substantially independent, identically distributed, partial scan data as input training data and the generated second substantially independent, identically distributed, partial scan data as label data to produce the trained machine learning-based system.

22. A medical image processing method, comprising:
receiving medical image data; and
performing denoising processing by applying the medical image data to a trained machine learning-based system, wherein the trained machine learning-based system is generated by (a) acquiring single scan data obtained from a single scan of a subject, the single scan data being count-domain projection data, (b) identically distributing the acquired single scan data to generate first and second substantially independent partial scan data, wherein the first partial scan data is generated by applying a thinning model to the projection data and the second partial scan data is generated by subtracting the generated first partial scan data from the projection data; and (c) training a machine learning-based system based on the generated first substantially independent, identically distributed, partial scan data as input training data and the generated second substantially independent, identically distributed, partial scan data as label data to produce the trained machine learning-based system.

* * * * *